United States Patent [19]

Mulvihill et al.

[11] Patent Number: 5,486,471

[45] Date of Patent: Jan. 23, 1996

[54] TISSUE PLASMINOGEN ACTIVATOR ANALOGS HAVING MODIFIED GROWTH FACTOR DOMAINS

[75] Inventors: Eileen R. Mulvihill, Seattle, Wash.; Shinji Yoshitake, Ibaraki, Japan; Yasunori Ikeda, Ibaraki, Japan; Suguru Suzuki, Ibaraki, Japan; Akira Hashimoto, Ibaraki, Japan; Teruaki Yuzuriha, Ibaraki, Japan; Bjorn A. Nexo, Søborg, Denmark

[73] Assignee: ZymoGenetics, Inc., Seattle, Wash.

[21] Appl. No.: 400,136

[22] Filed: Mar. 6, 1995

Related U.S. Application Data

[63] Continuation of Ser. No. 171,761, Dec. 22, 1993, abandoned, which is a continuation of Ser. No. 845,736, Mar. 2, 1992, abandoned, which is a continuation of Ser. No. 58,061, Jun. 4, 1987, abandoned.

[51] Int. Cl.$^6$ .................. C12N 9/64; C12N 1/21; C12N 5/10; A61K 38/49

[52] U.S. Cl. .................. 435/226; 124/94.64; 435/71.2; 435/240.2; 435/252.3; 435/252.31; 435/252.33; 435/254.11; 435/254.21; 435/254.3; 435/320.1; 536/23.2

[58] Field of Search .................. 424/94.64; 435/71.2, 435/240.2, 252.3, 252.31, 252.33, 254.11, 254.21, 254.3, 320.1; 536/23.2

[56] References Cited

U.S. PATENT DOCUMENTS

| | | | |
|---|---|---|---|
| 4,766,075 | 8/1988 | Goeddel et al. | 435/172.3 X |
| 4,908,204 | 3/1990 | Dodd et al. | 424/94.2 |
| 4,916,071 | 4/1990 | Hung et al. | 435/212 |
| 4,959,314 | 9/1990 | Mark et al. | 435/69.1 |

OTHER PUBLICATIONS van Zonneveld et al, *Proc. Natl Acad Sci*, USA, vol. 83, pp. 4670–4674, Jul. 1986.
Ny et al, *Proc. Natl. Acad Sci*, vol. 81, pp. 5355–5359, 1984.
Wang, et al, *Science*, vol. 224, pp. 1431–1433, 1984.

*Primary Examiner*—Mindy B. Fleisher
*Assistant Examiner*—Nancy T. Vogel
*Attorney, Agent, or Firm*—Seed and Berry

[57] ABSTRACT

Tissue plasminogen activator analogs containing the growth factor domain of native t-PA, the domain having at least one cysteine residue replaced with another amino acid. The t-PA analogs may further contain a variety of substitutions and/or modifications. Pharmaceutical compositions containing one or more of the t-PA analogs along With a physiologically acceptable carrier or diluent are also disclosed.

12 Claims, 30 Drawing Sheets

```
                10                              30                    45
AAGCTTGGAT CCACC ATG GAT GCA ATG AAG AGA GGG CTC TGC TGT GTG CTG CTG CTG
            MET Asp Ala MET Lys Arg Gly Leu Cys Cys Val Leu Leu Leu
            -35                 -30
    60              75              90              105
TGT GGC GCC GTC TTC GTT TCG CCC AGC CAG GAA ATC CAT GCC CGA TTC AGA AGA
Cys Gly Ala Val Phe Val Ser Pro Ser Gln Glu Ile His Ala Arg Phe Arg Arg
    -20                             -10
    120             135             150                 165
GGA GCC AGA TCT TAC CAA GTC ATC TGC AGA GAT GAA AAA ACG CAG ATG ATA TAC
Gly Ala Arg Ser Tyr Gln Val Ile Cys Arg Asp Glu Lys Thr Gln MET Ile Tyr
            1                           10
    180             195                 210
CAG CAA CAT CAG TCA TGG CTG CGC CCT GTG CTC AGA AGC AAC CGC CTG GAA TAT
Gln Gln His Gln Ser Trp Leu Arg Pro Val Leu Arg Ser Asn Arg Val Glu Tyr
                20                                  30
    225             240             255             270
TGC TGG TGC AAC AGT GGC AGG GCA CAG TGC CAC TCA GTG CCT GTC AAA AGT TGC
Cys Trp Cys Asn Ser Gly Arg Ala Gln Cys His Ser Val Pro Val Lys Ser Cys
                    40                                          50
        285             300             315
AGC CAG CCA AGG TGT TTC AAC GGG GGC ACC TGC CAG CAG GCC CTG TAC TTC TCA
Ser Glu Pro Arg Cys Phe Asn Gly Gly Thr Cys Gln Gln Ala Leu Tyr Phe Ser
                            60
330             345             360             375
GAT TTC GTG TGC CAG TGC CCC GAA GGA TTT GCT GGG AAG TGC TGT GAA ATA GAT
Asp Phe Val Cys Gln Cys Pro Glu Gly Phe Ala Gly Lys Cys Cys Glu Ile Asp
70                                              80
    390             405             420             435
ACC AGG GCC AGC TGC TAC GAG GAC CAG GGC ATC AGC TAC AGG GGC ACG TGG AGC
Thr Arg Ala Thr Cys Tyr Glu Asp Gln Gly Ile Ser Tyr Arg Gly Thr Trp Ser
        90                                      100
            450             465             480
ACA GCG GAG AGT GGC GCC GAG TGC ACC AAC TGG AAC AGC AGC GCG TTG GCC CAG
Thr Ala Glu Ser Gly Ala Glu Cys Thr Asn Trp Asn Ser Ser Ala Leu Ala Gln
                110                                 120
    495             510             525             540
AAG CCC TAC AGC GGG CGG AGG CCA CAC GCC ATC AGG CTG GGC CTG CGG AAC CAC
Lys Pro Tyr Ser Gly Arg Arg Pro Asp Ala Ile Arg Leu Gly Leu Gly Asn His
                    130                                         140
            555             570             585
AAC TAC TGC AGA AAC CCA GAT CGA GAC TCA AAG CCC TGG TGC TAC GTC TTT AAG
Asn Tyr Cys Arg Asn Pro Asp Arg Asp Ser Lys Pro Trp Cys Tyr Val Phe Lys
                                150
600             615             630             645
GCG GGG AAG TAC AGC TCA GAG TTC TGC AGC ACC CCT GCC TGC TCT GAG GGA AAC
Ala Gly Lys Tyr Ser Ser Glu Phe Cys Ser Thr Pro Ala Cys Ser Glu Gly Asn
160                                             170
        660             675             690             705
AGT GAC TGC TAC TTT GGG AAT GGG TCA GCC TAC CGT GGC ACG CAC AGC CTC ACC
Ser Asp Cys Tyr Phe Gly Asn Gly Ser Ala Tyr Arg Gly Thr His Ser Leu Thr
            180                                 190
```

*Fig. 1A*

```
                    720                    735                    750
GAG TCG CGT GCC TCC TGC CTC CCG TGG AAT TCC ATG ATC CTG ATA GCC AAG GTT
Glu Ser Gly Ala Ser Cys Leu Pro Trp Asn Ser MET Ile Leu Ile Gly Lys Val
                200                                            210
      765                    780                    795                    810
TAC ACA GCA CAG AAC CCC AGT GCC CAG GCA CTG GGC CTG GGC AAA CAT AAT TAC
Tyr Thr Ala Gln Asn Pro Ser Ala Gln Ala Leu Gly Leu Gly Lys His Asn Tyr
                            220                                            230
            825                    840                    855
TGC CGG AAT CCT CAT GGG GAT GCC AAG CCC TGG TGC CAC GTG CTG AAG AAC CGC
Cys Arg Asn Pro Asp Gly Asp Ala Lys Pro Trp Cys His Val Leu Lys Asn Arg
                                        240
870                    885                    900                    915
AGG CTG ACG TGG GAG TAC TGT GAT GTC CCC TCC TGC TCC ACC TGC GGC CTG AGA
Arg Leu Thr Trp Glu Tyr Cys Asp Val Pro Ser Cys Ser Thr Cys Gly Leu Arg
250                                            260
            930                    945                    960                    975
CAG TAC AGC CAG CCT CAG TTT CGC ATC AAA GGA GGG CTC TTC GCC GAC ATC GCC
Gln Tyr Ser Gln Pro Gln Phe Arg Ile Lys Gly Gly Leu Phe Ala Asp Ile Ala
                270                                            280
      990                    1005                   1020
TCC CAC CCC TGG CAG GCT GCC ATC TTT GCC AAG CAC AGG AGG TCG CCC GGA GAG
Ser His Pro Trp Gln Ala Ala Ile Phe Ala Lys His Arg Arg Ser Pro Gly Glu
                            290                                            300
      1035                   1050                   1065                   1080
CGG TTC CTG TGC GGC GGC ATA CTC ATC AGC TCC TGC TGG ATT CTC TCT GCC CCC
Arg Phe Leu Cys Gly Gly Ile Leu Ile Ser Ser Cys Trp Ile Leu Ser Ala Ala
                            310                                            320
            1095                   1110                   1125
CAC TGC TTC CAG GAG AGG TTT CCG CCC CAC CAC CTG ACG GTG ATC TTG GGC AGA
His Cys Phe Gln Glu Arg Phe Pro Pro His His Leu Thr Val Ile Leu Gly Arg
                                        330
1140                   1155                   1170                   1185
ACA TAC CGG GTG GTC CCT GGC GAG GAG GAG CAG AAA TTT GAA GTC GAA AAA TAC
Thr Tyr Arg Val Val Pro Gly Glu Glu Glu Gln Lys Phe Glu Val Glu Lys Tyr
340                                            350
            1200                   1215                   1230                   1245
ATT GTC CAT AAG GAA TTC GAT GAT GAC ACT TAC GAC AAT GAC ATT GCG CTG CTG
Ile Val His Lys Glu Phe Asp Asp Asp Thr Tyr Asp Asn Asp Ile Ala Leu Leu
                360                                            370
            1260                   1275                   1290
CAG CTG AAA TCG GAT TCG TCC CGC TGT GCC CAG GAG AGC AGC GTG GTC CGC ACT
Gln Leu Lys Ser Asp Ser Ser Arg Cys Ala Gln Glu Ser Ser Val Val Arg Thr
                            380                                            390
      1305                   1320                   1335                   1350
GTG TGC CTT CCC CCG GCG GAC CTG CAG CTG CCG GAC TGG ACG GAG TGT GAG CTC
Val Cys Leu Pro Pro Ala Asp Leu Gln Leu Pro Asp Trp Thr Glu Cys Glu Leu
                                  400                                            410
            1365                   1380                   1395
TCC GGC TAC GGC AAG CAT GAG GCC TTG TCT CCT TTC TAT TCG GAG CGG CTC AAG
Ser Gly Tyr Gly Lys His Glu Ala Leu Ser Pro Phe Tyr Ser Glu Arg Leu Lys
                                  420
```

*Fig. 1B*

```
1410                    1425                    1440                    1455
GAG GCT CAT GTC AGA CTG TAC CCA TCC AGC CCC TGC ACA TCA CAA CAT TTA CTT
Glu Ala His Val Arg Leu Tyr Pro Ser Ser Arg Cys Thr Ser Gln His Leu Leu
430                                         440
        1470                    1485                    1500                    1515
AAC AGA ACA GTC ACC GAC AAC ATG CTG TGT GCT GGA GAC ACT CGG AGC GGC GGG
Asn Arg Thr Val Thr Asp Asn MET Leu Cys Ala Gly Asp Thr Arg Ser Gly Gly
        450                                                 460
                1530                    1545                    1560
CCC CAG GCA AAC TTG CAC GAC GCC TGC CAG GCC CAT TCG GGA GGC CCC CTG GTG
Pro Gln Ala Asn Leu His Asp Ala Cys Gln Gly Asp Ser Gly Gly Pro Leu Val
                470                                                 480
    1575                    1590                    1605                    1620
TGT CTG AAC GAT GGC CGC ATG ACT TTG GTG GGC ATC ATC AGC TGG GGC CTG GGC
Cys Leu Asn Asp Gly Arg MET Thr Leu Val Gly Ile Ile Ser Trp Gly Leu Gly
                        490                                         500
                1635                    1650                    1665
TGT GGA CAG AAG GAT GTC CCG GGT GTG TAC ACC AAG GTT ACC AAC TAC CTA GAC
Cys Gly Gln Lys Asp Val Pro Gly Val Tyr Thr Lys Val Thr Asn Tyr Leu Asp
                                        510
1680                    1695                    1714        1724        1734
TGG ATT CGT GAC AAC ATG CGA CCG TGA CCAGGAACAC CCGACTCCTC AAAAGCAAAT GAGA
Trp Ile Arg Asp Asn MET Arg Pro
520                             527
```

*Fig. 1C*

```
              -35                            -30                                             -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                        -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                         20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                         40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                         60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                         80
Leu Tyr Phe Ser Asp Phe Val Cys Gln Cys Pro Glu Gly Phe Ala Gly Lys Ser Cys Glu
CTG TAC TTC TCA GAT TTC GTG TGC CAG TGC CCC GAA GGA TTT GCT GGG AAG AGC TGT GAA 90                                        100
Ile Asp Thr Arg Ala Thr Cys Tyr Glu Asp Gln Gly Ile Ser Tyr Arg Gly Thr Trp Ser
ATC GAT ACC AGG GCC ACG TGC TAC GAG GAC CAG GGC ATC AGC TAC AGG GGC ACG TGG AGC 110                                       120
Thr Ala Glu Ser Gly Ala Glu Cys Thr Asn Trp Asn Ser Ser Ala Leu Ala Gln Lys Pro
ACA GCG GAG AGT GGC GCC GAG TGC ACC AAC TGG AAC AGC AGC GCG TTG GCC CAG AAG CCC 130                                       140
Tyr Ser Gly Arg Arg Pro Asp Ala Ile Arg Leu Gly Leu Gly Asn His Asn Tyr Cys Arg
TAC AGC GGG CGG AGG CCA GAC GCC ATC AGC CTG GGC CTG GGG AAC CAC AAC TAC TGC AGA 150                                       160
Asn Pro Asp Arg Asp Ser Lys Pro Trp Cys Tyr Val Phe Lys Ala Gly Lys Tyr Ser Ser
AAC CCA GAT CGA GAC TCA AAG CCC TGG TGC TAC GTC TTT AAG GCG GGG AAG TAC AGC TCA 170                                       180
Glu Phe Cys Ser Thr Pro Ala Cys Ser Glu Gly Asn Ser Asp Cys Tyr Phe Gly Asn Gly
GAG TTC TGC AGC ACC CCT GCC TGC TCT GAG GGA AAC AGT GAC TGC TAC TTT GGG AAT GGG 190                                       200
Ser Ala Tyr Arg Gly Thr His Ser Leu Thr Glu Ser Gly Ala Ser Cys Leu Pro Trp Asn
TCA GCC TAC CGT GGC ACG CAC AGC CTC ACC GAG TCG GGT GCC TCC TGC CTC CCG TGG AAT 210                                       220
Ser Met Ile Leu Ile Gly Lys Val Tyr Thr Ala Gln Asn Pro Ser Ala Gln Ala Leu Gly
TCC ATG ATC CTG ATA GGC AAG GTT TAC ACA GCA CAG AAC CCC AGT GCC CAG GCA CTG GGC
```

*Fig. 4A*

```
                    230                                                240
Leu Gly Lys His Asn Tyr Cys Arg Asn Pro Asp Gly Asp Ala Lys Pro Trp Cys His Val
CTG GGC AAA CAT AAT TAC TGC CGG AAT CCT GAT GGG GAT GCC AAG CCC TGG TGC CAC GTG 250                                        260
Leu Lys Asn Arg Arg Leu Thr Trp Glu Tyr Cys Asp Val Pro Ser Cys Ser Thr Cys Gly
CTG AAG AAC CGC AGG CTG ACG TGG GAG TAC TGT GAT GTG CCC TCC TGC TCC ACC TGC GGC 270                                        280
Leu Arg Gln Tyr Ser Gln Pro Gln Phe Arg Ile Lys Gly Gly Leu Phe Ala Asp Ile Ala
CTG AGA CAG TAC AGC CAG CCT CAG TTT CGC ATC AAA GGA GGG CTC TTC GCC GAC ATC GCC 290                                        300
Ser His Pro Trp Gln Ala Ala Ile Phe Ala Lys His Arg Arg Ser Pro Gly Glu Arg Phe
TCC CAC CCC TGG CAG GCT GCC ATC TTT GCC AAG CAC AGG AGG TCG CCC GGA GAG CGG TTC 310                                        320
Leu Cys Gly Gly Ile Leu Ile Ser Ser Cys Trp Ile Leu Ser Ala Ala His Cys Phe Gln
CTG TGC GGG GGC ATA CTC ATC AGC TCC TGC TGG ATT CTC TCT GCC GCC CAC TGC TTC CAG 330                                        340
Glu Arg Phe Pro Pro His His Leu Thr Val Ile Leu Gly Arg Thr Tyr Arg Val Val Pro
GAG AGG TTT CCG CCC CAC CAC CTG ACG GTG ATC TTG GGC AGA ACA TAC CGG GTG GTC CCT 350                                        360
Gly Glu Glu Glu Gln Lys Phe Glu Val Glu Lys Tyr Ile Val His Lys Glu Phe Asp Asp
GGC GAG GAG GAG CAG AAA TTT GAA GTC GAA AAA TAC ATT GTC CAT AAG GAA TTC GAT GAT 370                                        380
Asp Thr Tyr Asp Asn Asp Ile Ala Leu Leu Gln Leu Lys Ser Asp Ser Ser Arg Cys Ala
GAC ACT TAC GAC AAT GAC ATT GCG CTG CTG CAG CTG AAA TCG GAT TCG TCC CGC TGT GCC 390                                        400
Gln Glu Ser Ser Val Val Arg Thr Val Cys Leu Pro Pro Ala Asp Leu Gln Leu Pro Asp
CAG GAG AGC AGC GTG GTC CGC ACT GTG TGC CTT CCC CCG GCG GAC CTG CAG CTG CCG GAC 410                                        420
Trp Thr Glu Cys Glu Leu Ser Gly Tyr Gly Lys His Glu Ala Leu Ser Pro Phe Tyr Ser
TGG ACG GAG TGT GAG CTC TCC GGC TAC GGC AAG CAT GAG GCC TTG TCT CCT TTC TAT TCG 430                                        440
Glu Arg Leu Lys Glu Ala His Val Arg Leu Tyr Pro Ser Ser Arg Cys Thr Ser Gln His
GAG CGG CTG AAG GAG GCT CAT GTC AGA CTG TAC CCA TCC AGC CGC TGC ACA TCA CAA CAT 450                                        460
Leu Leu Asn Arg Thr Val Thr Asp Asn Met Leu Cys Ala Gly Asp Thr Arg Ser Gly Gly
TTA CTT AAC AGA ACA GTC ACC GAC AAC ATG CTG TGT GCT GGA GAC ACT CGG AGC GGC GGG 470                                        480
Pro Gln Ala Asn Leu His Asp Ala Cys Gln Gly Asp Ser Gly Gly Pro Leu Val Cys Leu
CCC CAG GCA AAC TTG CAC GAC GCC TGC CAG GGC GAT TCG GGA GGC CCC CTG GTG TGT CTG
```

*Fig. 4B*

```
                    490                                              500
Asn Asp Gly Arg Met Thr Leu Val Gly Ile Ile Ser Trp Gly Leu Gly Cys Gly Gln Lys
AAC GAT GGC CGC ATG ACT TTG GTG GGC ATC ATC AGC TGG GGC CTG GGC TGT GGA CAG AAG 510                                              520        524
Asp Val Pro Gly Val Tyr Thr Lys Val Thr Asn Tyr Leu Asp Trp Ile Arg Asp Asn Met
GAT GTC CCG GGT GTG TAC ACA AAG GTT ACC AAC TAC CTA GAC TGG ATT CGT GAC AAC ATG

527
Arg Pro ---
CGA CCG TGA
```

*Fig. 4C*

```
                -35                      -30                                            -20
        Met Asp Ala Met Lys Arg Gly Leu Cys Cys Val Leu Leu Leu Cys Gly Ala Val Phe Val
        ATG GAT GCA ATG AAG AGA GGG CTC TGC TGT GTG CTG CTG CTG TGT GGC GCC GTC TTC GTT

-10                                 -1  +1
        Ser Pro Ser Gln Glu Ile His Ala Arg Phe Arg Arg Gly Ala Arg Ser Tyr Gln Val Ile
        TCG CCC AGC CAG GAA ATC CAT GCC CGA TTC AGA AGA GGA GCC AGA TCT TAC CAA GTG ATC 10                                      20
        Cys Arg Asp Glu Lys Thr Gln Met Ile Tyr Gln Gln His Gln Ser Trp Leu Arg Pro Val
        TGC AGA GAT GAA AAA ACG CAG ATG ATA TAC CAG CAA CAT CAG TCA TGG CTG CGC CCT GTG 30                                      40
        Leu Arg Ser Asn Arg Val Glu Tyr Cys Trp Cys Asn Ser Gly Arg Ala Gln Cys His Ser
        CTC AGA AGC AAC CGG GTG GAA TAT TGC TGG TGC AAC AGT GGC AGG GCA CAG TGC CAC TCA 50                                      60
        Val Pro Val Lys Ser Cys Ser Glu Pro Arg Cys Phe Asn Gly Gly Thr Cys Gln Gln Ala
        GTG CCT GTC AAA AGT TGC AGC GAG CCA AGG TGT TTC AAC GGG GGC ACC TGC CAG CAG GCC 70                                      80
        Leu Tyr Phe Ser Asp Phe Val Cys Gln Cys Pro Glu Gly Phe Ala Gly Lys Cys Ser Glu
        CTG TAC TTC TCA GAT TTC GTG TGC CAG TGC CCC GAA GGA TTT GCT GGG AAG TGC AGT GAA 90                                      100
        Ile Asp Thr Arg Ala Thr Cys Tyr Glu Asp Gln Gly Ile Ser Tyr Arg Gly Thr Trp Ser
        ATC GAT ACC AGG GCC ACG TGC TAC GAG GAC CAG GGC ATC AGC TAC AGG GGC ACG TGG AGC 110                                     120
        Thr Ala Glu Ser Gly Ala Glu Cys Thr Asn Trp Asn Ser Ser Ala Leu Ala Gln Lys Pro
        ACA GCG GAG AGT GGC GCC GAG TGC ACC AAC TGG AAC AGC AGC GCG TTG GCC CAG AAG CCC 130                                     140
        Tyr Ser Gly Arg Arg Pro Asp Ala Ile Arg Leu Gly Leu Gly Asn His Asn Tyr Cys Arg
        TAC AGC GGG CGG AGG CCA GAC GCC ATC AGG CTG GGC CTG GGG AAC CAC AAC TAC TGC AGA 150                                     160
        Asn Pro Asp Arg Asp Ser Lys Pro Trp Cys Tyr Val Phe Lys Ala Gly Lys Tyr Ser Ser
        AAC CCA GAT CGA GAC TCA AAG CCC TGG TGC TAC GTC TTT AAG GCG GGG AAG TAC AGC TCA 170                                     180
        Glu Phe Cys Ser Thr Pro Ala Cys Ser Glu Gly Asn Ser Asp Cys Tyr Phe Gly Asn Gly
        GAG TTC TGC AGC ACC CCT GCC TGC TCT GAG GGA AAC AGT GAC TGC TAC TTT GGG AAT GGG 190                                     200
        Ser Ala Tyr Arg Gly Thr His Ser Leu Thr Glu Ser Gly Ala Ser Cys Leu Pro Trp Asn
        TCA GCC TAC CGT GGC ACG CAC AGC CTC ACC GAG TCG GGT GCC TCC TGC CTC CCG TGG AAT 210                                     220
        Ser Met Ile Leu Ile Gly Lys Val Tyr Thr Ala Gln Asn Pro Ser Ala Gln Ala Leu Gly
        TCC ATG ATC CTG ATA GGC AAG GTT TAC ACA GCA CAG AAC CCC AGT GCC CAG GCA CTG GGC
```

*Fig. 5A*

```
                    230                                         240
Leu Gly Lys His Asn Tyr Cys Arg Asn Pro Asp Gly Asp Ala Lys Pro Trp Cys His Val
CTG GGC AAA CAT AAT TAC TGC CGG AAT CCT GAT GGG GAT GCC AAG CCC TGG TGC CAC GTG 250                                         260
Leu Lys Asn Arg Arg Leu Thr Trp Glu Tyr Cys Asp Val Pro Ser Cys Ser Thr Cys Gly
CTG AAG AAC CGC AGG CTG ACG TGG GAG TAC TGT GAT GTG CCC TCC TGC TCC ACC TGC GGC 270                                         280
Leu Arg Gln Tyr Ser Gln Pro Gln Phe Arg Ile Lys Gly Gly Leu Phe Ala Asp Ile Ala
CTG AGA CAG TAC AGC CAG CCT CAG TTT CGC ATC AAA GGA GGG CTC TTC GCC GAC ATC GCC 290                                         300
Ser His Pro Trp Gln Ala Ala Ile Phe Ala Lys His Arg Arg Ser Pro Gly Glu Arg Phe
TCC CAC CCC TGG CAG GCT GCC ATC TTT GCC AAG CAC AGG AGG TCG CCC GGA GAG CGG TTC 310                                         320
Leu Cys Gly Gly Ile Leu Ile Ser Ser Cys Trp Ile Leu Ser Ala Ala His Cys Phe Gln
CTG TGC GGG GGC ATA CTC ATC AGC TCC TGC TGG ATT CTC TCT GCC GCC CAC TGC TTC CAG 330                                         340
Glu Arg Phe Pro Pro His His Leu Thr Val Ile Leu Gly Arg Thr Tyr Arg Val Val Pro
GAG AGG TTT CCG CCC CAC CAC CTG ACG GTG ATC TTG GGC AGA ACA TAC CGG GTG GTC CCT 350                                         360
Gly Glu Glu Glu Gln Lys Phe Glu Val Glu Lys Tyr Ile Val His Lys Glu Phe Asp Asp
GGC GAG GAG GAG CAG AAA TTT GAA GTC GAA AAA TAC ATT GTC CAT AAG GAA TTC GAT GAT 370                                         380
Asp Thr Tyr Asp Asn Asp Ile Ala Leu Leu Gln Leu Lys Ser Asp Ser Ser Arg Cys Ala
GAC ACT TAC GAC AAT GAC ATT GCG CTG CTG CAG CTG AAA TCG GAT TCG TCC CGC TGT GCC 390                                         400
Gln Glu Ser Ser Val Val Arg Thr Val Cys Leu Pro Pro Ala Asp Leu Gln Leu Pro Asp
CAG GAG AGC AGC GTG GTC CGC ACT GTG TGC CTT CCC CCG GCG GAC CTG CAG CTG CCG GAC 410                                         420
Trp Thr Glu Cys Glu Leu Ser Gly Tyr Gly Lys His Glu Ala Leu Ser Pro Phe Tyr Ser
TGG ACG GAG TGT GAG CTC TCC GGC TAC GGC AAG CAT GAG GCC TTG TCT CCT TTC TAT TCG 430                                         440
Glu Arg Leu Lys Glu Ala His Val Arg Leu Tyr Pro Ser Ser Arg Cys Thr Ser Gln His
GAG CGG CTG AAG GAG GCT CAT GTC AGA CTG TAC CCA TCC AGC CGC TGC ACA TCA CAA CAT 450                                         460
Leu Leu Asn Arg Thr Val Thr Asp Asn Met Leu Cys Ala Gly Asp Thr Arg Ser Gly Gly
TTA CTT AAC AGA ACA GTC ACC GAC AAC ATG CTG TGT GCT GGA GAC ACT CGG AGC GGC GGG 470                                         480
Pro Gln Ala Asn Leu His Asp Ala Cys Gln Gly Asp Ser Gly Gly Pro Leu Val Cys Leu
CCC CAG GCA AAC TTG CAC GAC GCC TGC CAG GGC GAT TCG GGA GGC CCC CTG GTG TGT CTG
```

*Fig. 5B*

```
              490                                         500
Asn Asp Gly Arg Met Thr Leu Val Gly Ile Ile Ser Trp Gly Leu Gly Cys Gly Gln Lys
AAC GAT GGC CGC ATG ACT TTG GTG GGC ATC ATC AGC TGG GGC CTG GGC TGT GGA CAG AAG 510                                         520         524
Asp Val Pro Gly Val Tyr Thr Lys Val Thr Asn Tyr Leu Asp Trp Ile Arg Asp Asn Met
GAT GTC CCG GGT GTG TAC ACA AAG GTT ACC AAC TAC CTA GAC TGG ATT CGT GAC AAC ATG

527
Arg Pro ---
CGA CCG TGA
```

*Fig. 5C*

```
Cys Lys Thr Gly Asp Gly Lys Asn Tyr Arg Gly Thr Met Ser
TGC AAG ACC GGT GAT GGT AAA AAC TAC CGA GGT ACC ATG TCC

Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG

Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT

Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC

Asp Ile Leu Glu Cys
GAT ATC CTG GAA TGC
```

*Fig. 10*

```
        -35                      -30                                                  -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                           -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                          20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                          40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                          60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                          80
Leu Tyr Phe Ser Asp Phe Val Cys Gln Cys Pro Glu Gly Phe Ala Gly Lys Cys Cys Glu
CTG TAC TTC TCA GAT TTC GTG TGC CAG TGC CCC GAA GGA TTT GCT GGG AAG TGC TGT GAA 90                                         100
Ile Asp Thr Arg Ala Thr Cys Lys Thr Gly Asp Gly Lys Asn Tyr Arg Gly Thr Met Ser
ATA GAT ACG CGT GCC ACG TGC AAG ACC GGT GAT GGT AAA AAC TAC CGA GGT ACC ATG TCC 110                                         120
Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG 130                                         140
Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT 150                                         160
Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC 170                                         180
Asp Ile Leu Glu Cys Ser Glu Gly Asn Ser Asp Cys Tyr Phe Gly Asn Gly Ser Ala Tyr
GAT ATC CTG GAA TGC TCT GAG GGA AAC AGT GAC TGC TAC TTT GGG AAT GGG TCA GCC TAC 190                                         200
Arg Gly Thr His Ser Leu Thr Glu Ser Gly Ala Ser Cys Leu Pro Trp Asn Ser Met Ile
CGT GGC ACG CAC AGC CTC ACC GAG TCG GGT GCC TCC TGC CTC CCG TGG AAT TCC ATG ATC 210                                         220
Leu Ile Gly Lys Val Tyr Thr Ala Gln Asn Pro Ser Ala Gln Ala Leu Gly Leu Gly Lys
CTG ATA GGC AAG GTT TAC ACA GCA CAG AAC CCC AGT GCC CAG GCA CTG GGC CTG GGC AAA
```

*Fig. 16A*

```
                230                                              240
His Asn Tyr Cys Arg Asn Pro Asp Gly Asp Ala Lys Pro Trp Cys His Val Leu Lys Asn
CAT AAT TAC TGC CGG AAT CCT GAT GGG GAT GCC AAG CCC TGG TGC CAC GTG CTG AAG AAC 250                                              260
Arg Arg Leu Thr Trp Glu Tyr Cys Asp Val Pro Ser Cys Ser Thr Cys Gly Leu Arg Gln
CGC AGG CTG ACG TGG GAG TAC TGT GAT GTG CCC TCC TGC TCC ACC TGC GGC CTG AGA CAG 270                                              280
Tyr Ser Gln Pro Gln Phe Arg Ile Lys Gly Gly Leu Phe Ala Asp Ile Ala Ser His Pro
TAC AGC CAG CCT CAG TTT CGC ATC AAA GGA GGG CTC TTC GCC GAC ATC GCC TCC CAC CCC 290                                              300
Trp Gln Ala Ala Ile Phe Ala Lys His Arg Arg Ser Pro Gly Glu Arg Phe Leu Cys Gly
TGG CAG GCT GCC ATC TTT GCC AAG CAC AGG AGG TCG CCC GGA GAG CGG TTC CTG TGC GGG 310                                              320
Gly Ile Leu Ile Ser Ser Cys Trp Ile Leu Ser Ala Ala His Cys Phe Gln Glu Arg Phe
GGC ATA CTC ATC AGC TCC TGC TGG ATT CTC TCT GCC GCC CAC TGC TTC CAG GAG AGG TTT 330                                              340
Pro Pro His His Leu Thr Val Ile Leu Gly Arg Thr Tyr Arg Val Val Pro Gly Glu Glu
CCG CCC CAC CAC CTG ACG GTG ATC TTG GGC AGA ACA TAC CGG GTG GTC CCT GGC GAG GAG 350                                              360
Glu Gln Lys Phe Glu Val Glu Lys Tyr Ile Val His Lys Glu Phe Asp Asp Asp Thr Tyr
GAG CAG AAA TTT GAA GTC GAA AAA TAC ATT GTC CAT AAG GAA TTC GAT GAT GAC ACT TAC 370                                              380
Asp Asn Asp Ile Ala Leu Leu Gln Leu Lys Ser Asp Ser Ser Arg Cys Ala Gln Glu Ser
GAC AAT GAC ATT GCG CTG CTG CAG CTG AAA TCG GAT TCG TCC CGC TGT GCC CAG GAG AGC 390                                              400
Ser Val Val Arg Thr Val Cys Leu Pro Pro Ala Asp Leu Gln Leu Pro Asp Trp Thr Glu
AGC GTG GTC CGC ACT GTG TGC CTT CCC CCG GCG GAC CTG CAG CTG CCG GAC TGG ACG GAG 410                                              420
Cys Glu Leu Ser Gly Tyr Gly Lys His Glu Ala Leu Ser Pro Phe Tyr Ser Glu Arg Leu
TGT GAG CTC TCC GGC TAC GGC AAG CAT GAG GCC TTG TCT CCT TTC TAT TCG GAG CGG CTG 430                                              440
Lys Glu Ala His Val Arg Leu Tyr Pro Ser Ser Arg Cys Thr Ser Gln His Leu Leu Asn
AAG GAG GCT CAT GTC AGA CTG TAC CCA TCC AGC CGC TGC ACA TCA CAA CAT TTA CTT AAC 450                                              460
Arg Thr Val Thr Asp Asn Met Leu Cys Ala Gly Asp Thr Arg Ser Gly Gly Pro Gln Ala
AGA ACA GTC ACC GAC AAC ATG CTG TGT GCT GGA GAC ACT CGG AGC GGC GGG CCC CAG GCA 470                                              480
Asn Leu His Asp Ala Cys Gln Gly Asp Ser Gly Gly Pro Leu Val Cys Leu Asn Asp Gly
AAC TTG CAC GAC GCC TGC CAG GGC GAT TCG GGA GGC CCC CTG GTG TGT CTG AAC GAT GGC
```

*Fig. 16B*

```
              490                                           500
Arg Met Thr Leu Val Gly Ile Ile Ser Trp Gly Leu Gly Cys Gly Gln Lys Asp Val Pro
CGC ATG ACT TTG GTG GGC ATC ATC AGC TGG GGC CTG GGC TGT GGA CAG AAG GAT GTC CCG 510                                     520           524
Gly Val Tyr Thr Lys Val Thr Asn Tyr Leu Asp Trp Ile Arg Asp Asn Met Arg Pro ---
GGT GTG TAC ACA AAG GTT ACC AAC TAC CTA GAC TGG ATT CGT GAC AAC ATG CGA CCG TGA
```

*Fig. 16C*

```
        -35                         -30                                                -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                      -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                              20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                              40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                              60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                              80
Leu Tyr Phe Ser Asp Phe Val Cys Gln Cys Pro Glu Gly Phe Ala Gly Lys Cys Cys Glu
CTG TAC TTC TCA GAT TTC GTG TGC CAG TGC CCC GAA GGA TTT GCT GGG AAG TGC TGT GAA 90                                             100
Ile Asp Thr Arg Ala Thr Cys Lys Thr Gly Asp Gly Lys Asn Tyr Arg Gly Thr Met Ser
ATA GAT ACG CGT GCC ACG TGC AAG ACC GGT GAT GGT AAA AAC TAC CGA GGT ACC ATG TCC 110                                             120
Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG 130                                             140
Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT 150                                             160
Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC 170                                             180
Asp Ile Leu Glu Cys Ser Glu Gly Asn Ser Asp Cys Tyr Phe Gly Asn Gly Ser Ala Tyr
GAT ATC CTG GAA TGC TCT GAG GGA AAC AGT GAC TGC TAC TTT GGG AAT GGG TCA GCC TAC 190                                             200
Arg Gly Thr His Ser Leu Thr Glu Ser Gly Ala Ser Cys Leu Pro Trp Asn Ser Met Ile
CGT GGC ACG CAC AGC CTC ACC GAG TCG GGT GCC TCC TGC CTC CCG TGG AAT TCC ATG ATC 210                                             220
Leu Ile Gly Lys Val Tyr Thr Ala Gln Asn Pro Ser Ala Gln Ala Leu Gly Leu Gly Lys
CTG ATA GGC AAG GTT TAC ACA GCA CAG AAC CCC AGT GCC CAG GCA CTG GGC CTG GGC AAA
```

*Fig. 17A*

```
                        230                                          240
His Asn Tyr Cys Arg Asn Pro Asp Gly Asp Ala Lys Pro Trp Cys His Val Leu Lys Asn
CAT AAT TAC TGC CGG AAT CCT GAT GGG GAT GCC AAG CCC TGG TGC CAC GTG CTG AAG AAC 250                                          260
Arg Arg Leu Thr Trp Glu Tyr Cys Asp Val Pro Ser Cys Ser Thr Cys Gly Leu Arg Gln
CGC AGG CTG ACG TGG GAG TAC TGT GAT GTG CCC TCC TGC TCC ACC TGC GGC CTG AGA CAG 270                                          280
Tyr Ser Gln Pro Gln Phe Arg Ile Lys Gly Gly Leu Phe Ala Asp Ile Ala Ser His Pro
TAC AGC CAG CCT CAG TTT CGC ATC AAA GGA GGG CTC TTC GCC GAC ATC GCC TCC CAC CCC 290                                          300
Trp Gln Ala Ala Ile Phe Ala Lys His Arg Arg Ser Pro Gly Glu Arg Phe Leu Cys Gly
TGG CAG GCT GCC ATC TTT GCC AAG CAC AGG AGG TCG CCC GGA GAG CGG TTC CTG TGC GGG 310                                          320
Gly Ile Leu Ile Ser Ser Cys Trp Ile Leu Ser Ala Ala His Cys Phe Gln Glu Arg Phe
GGC ATA CTC ATC AGC TCC TGC TGG ATT CTC TCT GCC GCC CAC TGC TTC CAG GAG AGG TTT 330                                          340
Pro Pro His His Leu Thr Val Ile Leu Gly Arg Thr Tyr Arg Val Val Pro Gly Glu Glu
CCG CCC CAC CAC CTG ACG GTG ATC TTG GGC AGA ACA TAC CGG GTG GTC CCT GGC GAG GAG 350                                          360
Glu Gln Lys Phe Glu Val Glu Lys Tyr Ile Val His Lys Glu Phe Asp Asp Asp Thr Tyr
GAG CAG AAA TTT GAA GTC GAA AAA TAC ATT GTC CAT AAG GAA TTC GAT GAT GAC ACT TAC 370                                          380
Asp Asn Asp Ile Ala Leu Leu Gln Leu Lys Ser Asp Ser Ser Arg Cys Ala Gln Glu Ser
GAC AAT GAC ATT GCG CTG CTG CAG CTG AAA TCG GAT TCG TCC CGC TGT GCC CAG GAG AGC 390                                          400
Ser Val Val Arg Thr Val Cys Leu Pro Pro Ala Asp Leu Gln Leu Pro Asp Trp Thr Glu
AGC GTG GTC CGC ACT GTG TGC CTT CCC CCG GCG GAC CTG CAG CTG CCG GAC TGG ACG GAG 410                                          420
Cys Glu Leu Ser Gly Tyr Gly Lys His Glu Ala Leu Ser Pro Phe Tyr Ser Glu Arg Leu
TGT GAG CTC TCC GGC TAC GGC AAG CAT GAG GCC TTG TCT CCT TTC TAT TCG GAG CGG CTG 430                                          440
Lys Glu Ala His Val Arg Leu Tyr Pro Ser Ser Arg Cys Thr Ser Gln His Leu Leu Asn
AAG GAG GCT CAT GTC AGA CTG TAC CCA TCC AGC CGC TGC ACA TCA CAA CAT TTA CTT AAC 450                                          460
Arg Thr Val Thr Asp Asn Met Leu Cys Ala Gly Asp Thr Arg Ser Gly Gly Pro Gln Ala
AGA ACA GTC ACC GAC AAC ATG CTG TGT GCT GGA GAC ACT CGG AGC GGC GGG CCC CAG GCA 470                                          480
Asn Leu His Asp Ala Cys Gln Gly Asp Ser Gly Gly Pro Leu Val Cys Leu Asn Asp Gly
AAC TTG CAC GAC GCC TGC CAG GGC GAT TCG GGA GGC CCC CTG GTG TGT CTG AAC GAT GGC
```

*Fig. 17B*

```
              490                                          500
Arg Met Thr Leu Val Gly Ile Ile Ser Trp Gly Leu Gly Cys Gly Gln Lys Asp Val Pro
CGC ATG ACT TTG GTG GGC ATC ATC AGC TGG GGC CTG GGC TGT GGA CAG AAG GAT GTC CCG 510                                          520       524
Gly Val Tyr Thr Lys Val Thr Asn Tyr Leu Asp Trp Ile Arg Asp Asn Met Arg Pro ---
GGT GTG TAC ACA AAG GTT ACC AAC TAC CTA GAC TGG ATT CGT GAC AAC ATG CGA CCG TGA
```

Fig. 17C

20A  CRDEKTQMIYQQHQSWLRPVLRSNRVEYCWCNSGRAQC
20B  CFDNGKSYKIGETWERPYEGFMLSCTCLGNGSGRWQC
20C  CHDEKTGSSYKTGEQWERPYLSGNRLECTCLGNGRGEFRC
20D  CFDNGKSYKIGETWERPYEGFMLSCTCLGNGSGRWQC
20E  CFDNGKSYKTGEQWERPYLSGNRLECTCLGNGRGEFRC
20F  CFDNGKSYKTGEQWERPYLSGNRLECTCLGNGSGRWQC
20G  CHDEKTGSSYKIGETWERPYEGFMLSCTCLGNGRGEFRC
20H  CHDEKTGSSYKTGEQWERPYLSGNRLECTCLGNGRGEFRC
20I  CHDEKTGSSYKIGETWERPYEGFMLSCTCLGNGRGEFRC

Fig. 20

TISSUE PLASMINOGEN ACTIVATOR ANALOGS HAVING MODIFIED GROWTH FACTOR DOMAINS

CROSS-REFERENCES TO RELATED APPLICATIONS

This application is a continuation of U.S. patent application Ser. No. 08/171,761, filed Dec. 22, 1993, now abandoned; which was a continuation of U.S. patent application Ser. No. 07/845,736, filed Mar. 2, 1992, now abandoned; which was a continuation of U.S. patent application Ser. No. 07/058,061, filed Jun. 4, 1987.

TECHNICAL FIELD

The present invention relates to fibrinolytic agents, methods for their production, and pharmaceutical compositions containing them. More specifically, it relates to tissue plasminogen activator analogs having a modified growth factor domain.

BACKGROUND ART

Blood coagulation is a process consisting of a complex interaction of various blood components which eventually gives rise to a fibrin network, or clot. Degradation of the fibrin network can be accomplished by activation of the zymogen plasminogen into plasmin. Plasmin is a serine protease which acts directly to degrade the fibrin network and thereby regulate the coagulation process. Conversion of plasminogen into plasmin is normally catalyzed in vivo by tissue-type plasminogen activator (t-PA), a fibrin-specific serine protease which is believed to be the physiological vascular activator of plasminogen. Urokinase-type plasminogen activator (u-PA) is another member of the class of plasminogen activators characterized as serine proteases. t-PA and u-PA are functionally and immunologically distinguishable.

t-PA normally circulates as a single polypeptide chain of $M_r \approx 72,000$ daltons, which is converted to a two-chain form by cleavage of a peptide bond between amino acids 275 (Arg) and 276 (Ile). The heavy chain of t-PA (two variants of $M_r$ 40,000 and 37,000) is derived from the amino-terminus, while the light chain ($M_r$ 33,000) is derived from the carboxy-terminal end of the t-PA molecule. This cleavage is catalyzed by trypsin or plasmin, and is accompanied by an increase in activity, as measured using synthetic substrates, and by an increase in fibrinolytic activity. Single-chain t-PA becomes active upon binding to fibrin, probably due to a conformational change in the activator induced by binding to fibrin. Cleavage to the two-chain form may be associated with rapid clearance of t-PA from the bloodstream, but conflicting reports on this have been published (see Wallen et al., *Eur. J. Biochem.* 132: 681–686, 1983), and the clearance mechanism is poorly understood.

A two-dimensional model of the potential precursor t-PA protein has been established (Ny et al., *Proc. Natl. Acad. Sci. USA* 81: 5355–5359, 1984). From this model, it was determined that the heavy chain contains two triple disulfide structures known as "kringles." Similar kringle structures also occur in prothrombin, plasminogen and urokinase, and are believed to be important for binding to fibrin (Ny et al., ibid.). The second kringle (K2) of t-PA is believed to have a higher affinity for fibrin than the first kringle (K1) (Ichinose, Takio and Fujikawa, *Journal of Clinical Investigation* 78;163–169, 1986; Verheijen et al., *EMBO J.* 5: 3525–3530, 1986).

In addition, the heavy chain of t-PA contains a "growth factor" domain, a triple disulfide-bonded structure which has homology to epidermal growth factor and to similar domains in protein C, factor VII, factor IX and factor X.

The heavy chain of t-PA also contains a "finger" domain that is homologous to the finger domains of fibronectin. Fibronectin exhibits a variety of biological activities, including fibrin binding; its fibrin-binding activity has been correlated to four or five of its nine finger domains.

The light chain of t-PA contains the active site for serine protease activity, which is highly homologous to the active sites of other serine proteases.

The precursor form of t-PA additionally comprises a pre-region followed downstream by a pro-region, which are collectively referred to as the "pre-pro" region. The pre-region contains a signal peptide which is important for secretion of t-PA by vascular endothelial cells (Ny et al., ibid.). The pre sequence is believed responsible for secretion of t-PA into the lumen of the endoplasmic reticulum, a necessary step in extracellular secretion. The pro sequence is believed to be cleaved from the t-PA molecule following transport from the endoplasmic reticulum to the Golgi apparatus.

The use of t-PA for fibrinolysis in animal and human subjects has highlighted several shortcomings of the native molecule. The half-life of t-PA in vivo has been shown to be as short as three minutes in humans (Nilsson et al., *Scand. J. Haematol.* 33: 49–53, 1984). Injected t-PA is rapidly cleared by the liver, and, within 30 minutes, most of the injected material is metabolized to low molecular weight forms. This short half-life may limit the effectiveness of t-PA as a thrombolytic agent by necessitating high dosages. Typically, native t-PA is administered at a dose of 30 to 150 mg per patient, and the low solubility of the protein necessitates prolonged infusion. Fuchs et al. (*Blood* 65: 539–544, 1985) concluded that infused t-PA is cleared by the liver in a process independent of the proteolytic site and that infused t-PA will not accumulate in the body; that is, the clearance mechanism cannot be saturated. Furthermore, doses of t-PA sufficient to lyse coronary thrombi are far larger than normal physiological levels, and may cause activation of plasminogen throughout the body, leading to systemic degradation of fibrinogen (Sherry, ibid.), which results in dangerous bleeding episodes. This systemic activity is apparently due to the low specificity of the two-chain form of the molecule.

Various workers have modified t-PA in attempts to enhance its clinical suitability. Rosa and Rosa (International Patent Application WO 86/01538) modified the Lys at position 277 of t-PA to stabilize the single-chain form of t-PA. Ile (277) t-PA produced in *E. coli* was found to be less active as a single-chain molecule, as compared to native t-PA. Wallen et al. (ibid.) postulated that this lysine residue may be responsible for proteolytic activity of single-chain t-PA. Heyneker and Vehar (published British Patent Application 2,173,804) disclose amino acid substitutions around the cleavage site of t-PA. A variant t-PA comprising Glu at position 275 was shown to have greater specific activity, as compared to native t-PA. This variant t-PA also formed fewer complexes with t-PA inhibitor. The single-chain form was also shown to have greater affinity for fibrin than the two-chain form. Robinson (WO 84/01786) used enzymatic means to remove carbohydrate side chains from t-PA to increase plasma half-life. Van Zonneveld et al. (*Proc. Natl. Acad. Sci. USA* 83: 4670–4674, 1986) disclose modified forms of t-PA wherein portions of the heavy chain have been deleted. Robinson et al. (EP 207,589 A1) disclose mutant forms of t-PA in which the growth factor domain has been deleted or otherwise modified. However, these variant forms of t-PA do not fully overcome the problems associated with the native protein.

There remains a need in the art for a plasminogen-activating protein with a long half-life and high specificity for fibrin. The present invention fulfills this need by providing novel derivatives of tissue plasminogen activator in which the growth factor domain has been structurally disrupted. The t-PA analogs described herein provide significant advantages over native t-PA as therapeutic fibrinolytic agents by permitting the use of much smaller doses, thus overcoming the problems of low solubility of native t-PA and permitting administration by injection rather than infusion. Through the use of recombinant DNA technology, a consistent and homogeneous source of these proteins is provided. The proteins can be utilized to lyse existing clots in heart attack and stroke victims and in others where the need to lyse or suppress the formation of fibrin matrices is therapeutically desirable.

DISCLOSURE OF THE INVENTION

Briefly stated, the present invention discloses tissue plasminogen activator analogs containing the growth factor domain of native t-PA, the domain having at least one cysteine residue replaced with another amino acid. Within selected embodiments of the present invention, the cysteine residue is no. 83 or no. 84 of native t-PA, and the amino acid is serine or alanine. Within a particularly preferred embodiment, the cysteine residue is no. 84 of native t-PA and the amino acid is serine.

The t-PA analogs described herein may further contain a substitution of at least one amino acid within thirteen amino acid residues of the cleavage site, this substitution resulting in an increased resistance to cleavage by plasmin. In addition, the t-PA analogs described herein may contain a finger domain having an amino acid sequence selected from the group consisting of the sequences set forth in FIG. 20(A)–(I).

Within other aspects of the present invention, the analog contains two kringle structures, at least one of which lacks carbohydrate. In addition, the analogs described herein may contain a kringle structure derived from plasminogen. Within preferred embodiments, the plasminogen kringle structure is selected from the group consisting of the K1, K4 and K5 kringle domains of plasminogen. In addition to the plasminogen kringle structure, the t-PA analogs may further contain the K2 kringle structure of native t-PA positioned downstream of the plasminogen kringle structure.

Within a related aspect of the present invention, t-PA analogs are disclosed which contain a growth factor domain of a protein selected from the group consisting of protein C, factor VII, factor IX and factor X. These analogs may further include the substitutions and other modifications described above.

DNA sequences encoding the t-PA analogs described above, as well as expression vectors containing such DNA sequences, are also disclosed. Preferred expression vectors in this regard are Zem99-9100 or Zem99-9200.

Host cells transfected or transformed with such an expression vector are also disclosed. The host cell may be *E. coli* or a mammalian host cell, such as BHK host cells.

Still another aspect of the present invention discloses pharmaceutical compositions comprising a t-PA analog as described herein, and a physiologically acceptable carrier or diluent.

These and other aspects of the present invention will become evident upon reference to the following detailed description and attached drawings.

BRIEF DESCRIPTION OF THE DRAWINGS

FIG. 1 illustrates the pre-pro t-PA coding sequence constructed from cDNA and synthesized oligonucleotides, together with the amino acid sequence of the encoded protein. Numbers above the lines refer to nucleotide position and numbers below the lines refer to amino acid position.

FIG. 4 illustrates the nucleotide sequence of the mutant DNA sequence in Zem99-9100, together with the amino acid sequence of the encoded t-PA analog. Numbers refer to amino acid position.

FIG. 5 illustrates the nucleotide sequence of the mutant DNA sequence in Zem99-9200, together with the amino acid sequence of the encoded t-PA analog. Numbers refer to amino acid position.

FIG. 10 illustrates the amino acid sequence and DNA sequence of the K1 domain of plasminogen.

FIGS. 16 and 17 show the cDNA sequences and amino acid sequences of representative t-PA analogs.

FIG. 20(A)–(I) illustrates the amino acid sequences of the finger domain of native t-PA and of consensus finger domains.

BEST MODE FOR CARRYING OUT THE INVENTION

Figure 2:
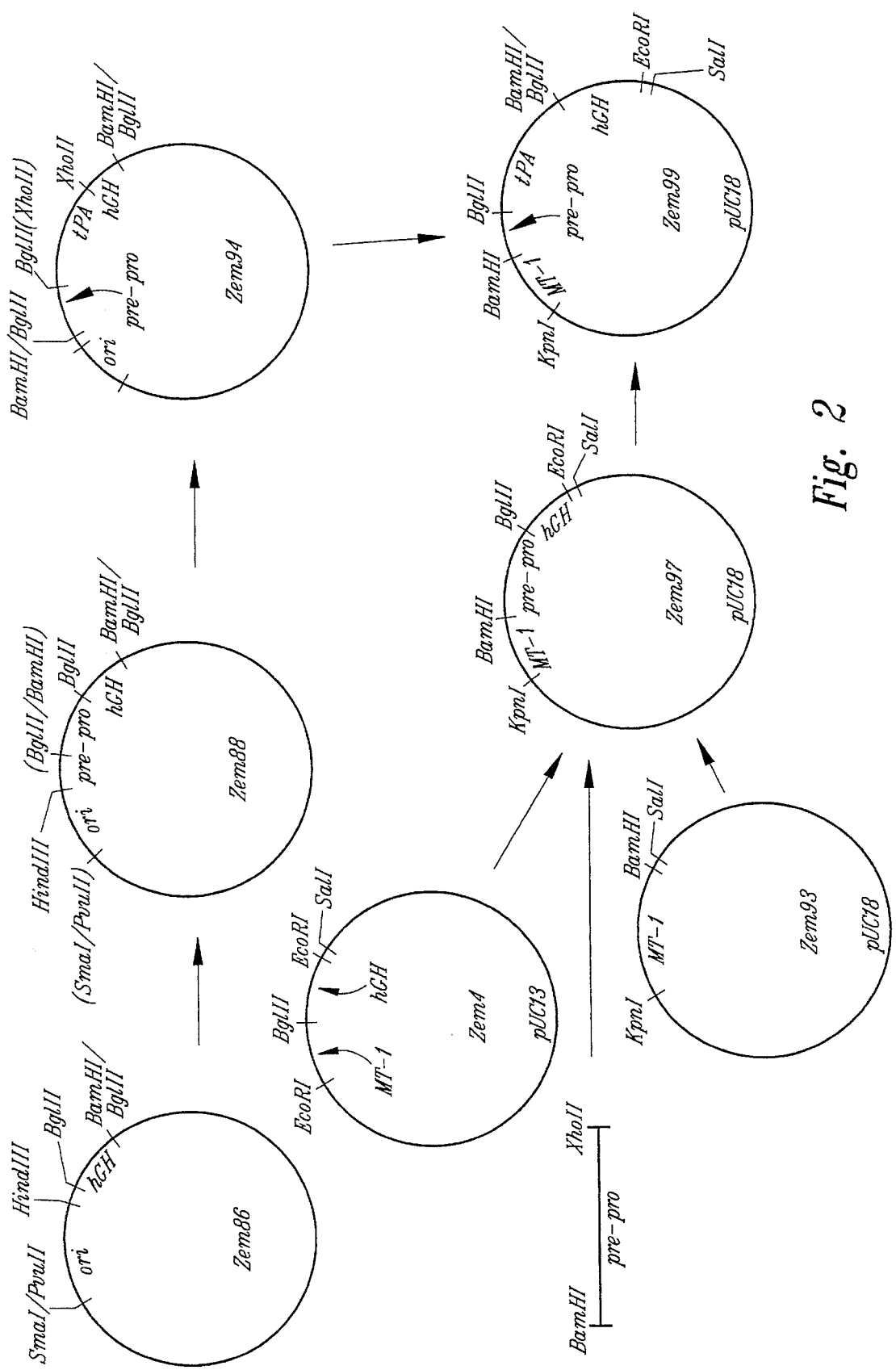
FIG. 2 illustrates the construction of the vector Zem99.

Prior to setting forth the invention, it may be helpful to an understanding thereof to set forth definitions of certain terms used herein.

Complementary DNA or cDNA

A DNA molecule or sequence which has been enzymatically synthesized from the sequences present in an mRNA template, or a clone of such a molecule.

DNA Construct

A DNA molecule, or a clone of such a molecule, either single- or double-stranded, which has been modified through human intervention to contain segments of DNA combined and juxtaposed in a manner which would not otherwise exist in nature.

Plasmid or Vector

A DNA construct containing genetic information which provides for its replication when inserted into a host cell. Replication may be autonomous or achieved by integration into the host genome. A plasmid generally contains at least one gene sequence to be expressed in the host cell, as well as sequences which encode functions that facilitate such gene expression, including promoters, transcription initiation sites, and transcription terminators. It may be a linear molecule or a closed, circular molecule.

Pre-Pro Region

An amino acid sequence which generally occurs at the amino-termini of the precursors of certain proteins, and which is generally cleaved from the protein, at least in part, during secretion. The pre-pro region comprises, in part, sequences directing the protein into the secretory pathway of the cell, and generally contains a region which is rich in hydrophobic amino acids.

Domain

A three-dimensional, self-assembling array of amino acids of a protein molecule, which contains structural elements necessary for a specific biological activity of that protein.

Biological Activity

The function or set of functions performed by a molecule in a biological context (i.e., in an organism, a cell, or an in vitro facsimile thereof). Biological activities of proteins may be divided into catalytic and effector activities. Catalytic activities of fibrinolytic agents often involve the activation of other proteins through specific cleavage of precursors. In contrast, effector activities include specific binding of the biologically active molecule to other molecules, such as fibrin, or to cells. Effector activity frequently augments, or is essential to, catalytic activity under physiological conditions. Catalytic and effector activities may, in some cases, reside in the same domain of the protein. For plasminogen activators, biological activity is characterized by the conversion of the pro-enzyme or zymogen plasminogen into plasmin, which in turn degrades fibrin matrices. Because fibrin acts as a cofactor in the activation of plasminogen by t-PA, single chain t-PA has relatively little activity in the absence of fibrin.

Native t-PA

A protein having the structure and biological activity of tissue plasminogen activator as isolated from human melanoma cells (see EP 0041766 A2). Native t-PA has the amino acid sequence of the melanoma cell t-PA, or may contain slight variations in sequence. Such variations, arising from, for example, genetic polymorphisms, will not substantially alter the structure or activity of the protein. Native t-PA may be isolated from cells which naturally produce it, or may be prepared from recombinant cells which have been transfected or transformed with a DNA sequence encoding native t-PA. The amino acid sequence of a representative native t-PA is shown in FIG. 1.

t-PA Analog

A protein having the characteristic biological activity of plasminogen activators as defined above, further characterized by the presence of a specific artificially induced mutation in the amino acid sequence. The DNA sequence encoding a t-PA analog is referred to as a "mutant DNA sequence," and will generally be in the form of a cDNA. The term "specific artificially induced mutation" includes deletions, insertions and substitutions in the amino acid sequence, which may be introduced through manipulation of a cloned DNA sequence. In general, the biological activity of the t-PA analogs will be measurably altered from that of native t-PA.

As noted above, human t-PA is a 72,000 dalton protein which may exist in a two-chain form. The entire mature protein contains 35 cysteine residues, 34 of which participate in inter- or intrachain disulfide bonds (Ny et al., ibid.). Seven of these cysteines are within the region of the molecule referred to as the "growth factor domain" (hereinafter "GF domain") and are arranged in three disulfide bonds, with the seventh cysteine remaining unpaired.

Also as noted above, the GF domain has been found to be responsible for certain limitations in the use of native t-PA as a pharmaceutical agent. Investigations by the inventors have produced data indicating that the GF domain may be partially responsible for the rapid clearing of t-PA from the bloodstream. Furthermore, the presence of a free sulfhydryl group in the GF domain may destabilize the protein. In general, free sulfhydryl groups of proteins in solution tend to be oxidized spontaneously, and may also form intermolecular disulfide bridges, leading to protein aggregation. When a protein having a free sulfhydryl group is used as a pharmaceutical agent, these changes in physiochemical properties, resulting from free sulfhydryl groups, may alter the immunogenic or antigenic properties of the protein and therefore limit its therapeutic utility. This effect has been observed for interleukin-2 (Wang et al., *Science* 224: 1431–1433, 1984. and Liang et al., *J. Biol. Chem.* 261: 334–337, 1986).

The inventors have discovered that by eliminating a cysteine residue from the GF domain of t-PA, the in vivo half-life of the protein is prolonged. Preferably, the cysteine residue at position 84 is removed, although the other cysteine residues at positions 51, 56, 62, 73, 75 and 83 may also be removed, either singly or in combination. In any event, it is preferable that the resulting molecule not have an unpaired cysteine, for reasons discussed above. Cysteine residues may be removed by deletion or amino acid substitution, with substitution being the preferred method. In principle, any amino acid may be substituted for cysteine, although serine and alanine are preferred. A particularly preferred substitute amino acid is serine.

The t-PA analogs of the present invention may contain the GF domain of native t-PA, altered at at least one cysteine residue, or may contain a GF domain derived from another protein. In particular, it may be advantageous to substitute a GF domain from a protein known to have a long in vivo half-life, such as protein C, factor VII, factor IX or factor X. DNA sequences encoding these proteins have been described (see, for example, Hagen et al., EP 200,421; Foster et al., *Proc. Natl. Acad. Sci. USA* 82: 4673–4677, 1985; Kurachi and Davie, *Proc. Natl. Acad. Sci. USA* 79: 6461–6464, 1982; and Leytus et al., *Biochemistry* 25: 5098–5102, 1986). By digesting the respective DNA sequences with appropriate restriction enzymes, the necessary fragments with which to construct such hybrid coding sequences may be obtained. Conventional laboratory techniques, such as oligonucleotide synthesis, oligonucleotide-directed mutagenesis and enzymatic ligation, may also be employed to join the component sequences in the proper reading frame.

In addition to the substitution(s) for cysteine(s) in the GF domain, the t-PA analogs of the present invention may contain additional mutations. These mutations may be amino acid substitutions, deletions or additions. Many such mutations have been described, as discussed above. Particularly preferred mutations include substitutions of the finger and/or K1 domains, amino acid substitutions near the cleavage (activation) site, the removal of the carbohydrate attachment site in the K1 domain or the modification of the carbohydrate attachment site in the K2 domain. Such mutations will enhance the clinical suitability of the t-PA analogs. For example, the K1 domain of native t-PA may be replaced with a kringle domain derived from another protein to enhance the fibrin specificity of the resulting analog. Suitable kringle domains in this regard include the K1, K2, K3, K4 and K5 domains of plasminogen, the K2 domain of native t-PA, the K1 and K2 domains of prothrombin, and the kringle domain of factor XII. The K1 domain of plasminogen is particularly preferred. In addition, modifications to the finger domain and the activation site will increase clot specificity of the t-PA analog. Modifications of carbohydrate attachment sites increase the uniformity of the protein product and increase plasma half-life.

According to the present invention, it is preferred to produce these novel proteins through the use of recombinant DNA technology, using cDNA clones or genomic clones as starting materials. Suitable DNA sequences can also be synthesized according to standard procedures. It is preferred to use cDNA clones because, by employing the full-length cDNA encoding native t-PA as starting material for producing modified t-PA, introns are removed so that all exons of the native t-PA are present and correctly oriented with respect to one another. The cDNA can also be used as a template for deletion, alteration or insertion of sequences via oligonucleotide-directed mutagenesis.

Recombinant DNA technology allows the convenient enhancement of the fibrin-binding domain of native t-PA. Such enhancements may be achieved by the insertion of additional kringle structures, modification of kringle structures, the addition of finger domains, or the substitution of the finger domain. This methodology provides a means for selecting the optimum combination of functional domains found in native t-PA or in related proteins, and thus provides fibrinolytic agents with enhanced biological activity with respect to fibrin binding and specificity of serine protease activity.

Amino acid substitutions or deletions are introduced by site-specific mutagenesis using the cloned t-PA sequence or a portion thereof as a template. Techniques for oligonucleotide-directed in vitro mutagenesis are generally known in the art. A preferred such method is that of Zoller and Smith, *DNA* 3: 479–488, 1984. Oligonucleotides may be synthesized by standard procedures, including automated machine synthesis, or may be obtained from commercial sources. The mutated sequence is then joined to the remainder of the t-PA coding sequence, and the reconstructed coding sequence is then inserted into an expression vector. The mutant sequences may be expressed in various host cells, including mammalian cells, yeast and other fungi, and bacteria.

Production of recombinant t-PA in bacteria, yeast and mammalian cells is disclosed by, for example, Goeddel et al. (EP 93619 A1), Meyhack and Hinnen (EP 143,081 A2), and Gill (EP 174,835 A1). Methods for transfecting mammalian cells and for transforming bacteria and fungi with foreign DNA are well known in the art. Suitable expression vectors will comprise a promoter which is capable of directing the transcription of a foreign gene in a host cell and a functional transcription termination site.

In some instances, it is preferred that expression vectors further comprise an origin of replication, as well as sequences which regulate and/or enhance expression levels, depending on the host cell selected. Suitable expression vectors may be derived from plasmids, RNA and DNA viruses or cellular DNA sequences, or may contain elements of each.

Preferred prokaryotic hosts for use in carrying out the present invention are strains of the bacteria *Escherichia coli*, although *Bacillus* and other genera are also useful. Techniques for transforming these hosts, and for expressing foreign DNA sequences cloned in them, are well known in the art (see, for example, Maniatis et al., *Molecular Cloning: A Laboratory Manual*, Cold Spring Harbor Laboratory, 1982). Vectors used for expressing foreign DNA in bacterial hosts will generally contain a selectable marker, such as a gene for antibiotic resistance, and a promoter which functions in the host cell. Appropriate promoters include the trp (Nichols and Yanofsky, *Meth. in Enzymology* 101: 155, 1983), lac (Casadaban et al., *J. Bact.* 143: 971–980, 1980), TAC (Russell et al., *Gene* 20: 231–243, 1982), and phage λ promoter systems. Plasmids useful for transforming bacteria include pBR322 (Bolivar et al., *Gene* 2: 95–113, 1977), the pUC plasmids (Messing, *Meth. in Enzymology* 101: 20–77, 1983; and Vieira and Messing, *Gene* 19: 259–268, 1982), pCQV2 (Queen, *J. Mol. Appl. Genet.* 2: 1–10, 1983), and derivatives thereof.

Eukaryotic microorganisms, such as the yeast *Saccharomyces cerevisiae*, or filamentous fungi including *Aspergillus*, may also be used as host cells. Particularly preferred species of *Aspergillus* include *A. nidulans, A. niger, A. oryzae,* and *A. terreus.* Techniques for transforming yeast are described by, for example, Beggs (*Nature* 275: 104–108, 1978). *Aspergillus* species may be transformed according to known procedures, for example, that of Yelton et al. (*Proc. Natl. Acad. Sci. USA* 81: 1740–1747, 1984). Expression vectors for use in yeast include YRp7 (Struhl et al., *Proc. Natl. Acad. Sci. USA* 76: 1035–1039, 979), YEp13 (Broach et al., *Gene* 8: 121–133, 1979), pJDB248 and pJDB219 (Beggs, ibid.), and derivatives thereof. Such vectors will generally comprise a selectable marker, such as the nutritional marker TRP1, which allows selection in a host strain carrying a trp1 mutation. Preferred promoters for use in yeast expression vectors include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599, 311) or alcohol dehydrogenase genes (Young et al., in *Genetic Engineering of Microorganisms for Chemicals,* Hollaender et al., eds., p. 335, Plenum, New York, 1982; and Ammerer, *Meth. in Enzymology* 101: 192–201, 1983). To facilitate purification of a modified t-PA protein produced in a yeast transformant and to obtain proper disulphide bond formation, a signal sequence from a yeast gene encoding a secreted protein may be substituted for the t-PA pre-pro sequence. A particularly preferred signal sequence is the pre-pro region of the MFα1 gene (Kurjan and Herskowitz, *Cell* 30: 933–943, 1982; and Singh (EP 123,544)).

Higher eukaryotic cells may also serve as host cells in carrying out the present invention. Cultured mammalian cells, such as the BHK, CHO, NS-1, SP2/0 and J558L cell lines, are preferred. These and other cell lines are widely available, for example, from the American Type Culture Collection. A particularly preferred adherent cell line is the BHK cell line tk⁻ts13 (Waechter and Baserga, *Proc. Natl. Acad. Sci. USA* 79: 1106–1110, 1982), hereinafter referred to as "tk⁻BHK cells." Expression vectors for use in mammalian cells will comprise a promoter capable of directing the transcription of a foreign gene introduced into a mammalian cell. Particularly preferred promoters include the SV40 promoter (Subramani et al., *Mol. Cell Biol.* 1: 854–64, 1981), the MT-1 promoter (Palmiter et al., *Science* 222: 809–814, 1983), and the mouse kappa gene promoter (Bergman et al., *Proc. Natl. Acad. Sci. USA* 81: 7041–7045, 1984). Also contained in the expression vectors is a transcription terminator, located downstream of the insertion site for the DNA sequence to be expressed. A preferred terminator is the human growth hormone (hGH) gene terminator (DeNoto et al., *Nuc. Acids Res.* 9: 3719–3730, 1981). In addition, vectors will preferably contain enhancer sequences appropriate to the particular host cell line.

For expression of mutant t-PAs in cultured mammalian cells, expression vectors containing cloned t-PA sequences are introduced into the cells by appropriate transfection techniques, such as calcium phosphate-mediated transfection (Graham and Van der Eb, *Virology* 52: 456–467, 1973; as modified by Wigler et al., *Proc. Natl. Acad. Sci. USA* 77: 3567–3570, 1980; or as described by Loyter et al., *Proc. Natl. Acad. Sci. USA* 79: 422, 1982) or electropotation (Neumann et al., *EMBO J.* 1: 841–845, 1982). A portion of the cells take up the DNA and maintain it inside the cell for several days. A small fraction of the cells integrate the DNA into the genome of the host cell or maintain the DNA in non-chromosomal nuclear structures. These transfectants can be identified by cotransfection with a gene that confers a selectable phenotype (a selectable marker). Preferred selectable markers include the DHFR gene, which imparts cellular resistance to methotrexate (MTX), an inhibitor of nucleotide synthesis; or the bacterial neomycin resistance gene, which confers resistance to the drug G-418, an inhibitor of protein synthesis. After the host cells have taken up the DNA, drug selection is applied to select for a population of cells that are expressing the selectable marker at levels high enough to confer resistance. Selectable markers may be carried on the same vector as the sequence encoding the t-PA analog, or may be carried on a separate vector.

Coamplification as a means to increase expression levels can be accomplished by the addition of high concentrations of MTX to the culture medium at the time of the initial selection, or can be subsequently accomplished by sequentially increasing the concentration of MTX in the medium, followed by repeated cloning by dilution of the drug-resistant cell lines. Variations exist in the ability to amplify and relate both to the initial genomic configuration (i.e., extra-chromosomal vs. chromosomal) of the cotransfected DNA sequences and to the mechanism of amplification itself, in which variable amounts of DNA rearrangements can occur. This is noticed upon further amplification of clones which have been previously shown to be stable. For this reason, it is necessary to clone by dilution after every amplification step. Cells which express the DHFR marker are then selected and screened for production of t-PA. Screening may be done by enzyme-linked immunosorbent assay (ELISA) or by biological activity assays.

The mutant t-PAs of the present invention exhibit a fibrinolytic effect which is equivalent to that of native t-PA. However, these proteins exhibit an advantage over native t-PA in that they may have a plasma half-life as much as five times as long as that of native t-PA, suggesting that they may be superior therapeutic agents.

The t-PA analogs of the present invention may be used within pharmaceutical compositions for the treatment of thrombosis. The pharmaceutical compositions will comprise the t-PA analogs in combination with a carrier or diluent, such as sterile water or sterile saline, and may also comprise appropriate excipients and/or solvents. The resulting aqueous solutions may be packaged for use or filtered under aseptic conditions and lyophilized, the lyophilized preparation being combined with a sterile aqueous solution prior to administration.

Typically, an aqueous solution containing 3 g of mannitol and $10^6$ units of the t-PA analog is prepared under sterile conditions. One ml aliquots of this solution are pipetted into small vials, which are then lyophilized and sealed. For injection, the lyophilized material is combined with 2 ml of sterile water, the water being provided in a sealed ampoule. Administration is preferably by injection. The proteins of the present invention will typically be administered at doses of from about 6 mg to about 30 mg per patient, depending on the weight of the patient and the nature of the thrombus to be dissolved. However, the present invention is not restricted to the above range and the dose may be varied depending on the condition. Determination of proper dose will be apparent to the skilled practitioner.

The following examples are offered by way of illustration, and not by way of limitation.

EXAMPLES

EXAMPLE 1

Construction of a Full-Length t-PA Clone

The sequence of a native human t-PA cDNA clone has been reported (Pennica et al., *Nature* 301: 214–221, 1983). The sequence encodes a pre-pro peptide of 32–35 amino acids followed by a 527–530 amino acid mature protein.

A cDNA clone comprising the coding sequence for mature t-PA was constructed using as starting material mRNA from the Bowes melanoma cell line (Rijken and Collen, *J. Biol. Chem.* 256: 7035–7041, 1981). This cDNA was then used to construct the plasmid pDR1296. *Escherichia coli* strain JM83 transformed with pDR1296 has been deposited with the American Type Culture Collection under Accession No. 53347.

Because the pre-pro sequence was not present in the cDNA clone pDR1296, it was constructed from synthesized oligonucleotides and subsequently joined to the cDNA. In the synthesized t-PA pre-pro sequence, cleavage sites for Bam HI and Nco I were introduced immediately 5' to the first codon (ATG) of the pre-pro sequence, and a Bgl II (Sau 3A, Xho II) site was maintained at the 3' end of the pre-pro sequence. The naturally-occurring pre-pro sequence lacks a convenient restriction site near the middle; however, the sequence GGAGCA (coding for amino acids −20 and −19, Gly-Ala) can be altered to GGCGCC to provide a Nar I site without changing the amino acid sequence.

To construct the pre-pro sequence, the following oligonucleotides were synthesized using an Applied Biosystems Model 380-A DNA synthesizer:

| | |
|---|---|
| ZC131: | 5'GGA TCC ATG GAT GCA ATG AAG AGA GGG CTC TGC TGT GTG3' |
| ZC132: | 5'TGG CGC CAC ACA GCA GCA GCA CAC AGC AGAG3' |
| ZC133: | 5'GGC GCC GTC TTC GTT TCG CCC AGC CAG GAA ATC CATG3' |
| ZC134: | 5'AGA TCT GGC TCC TCT TCT GAA TCG GGC ATG GAT TTC CT3' |

Following purification, oligomers ZC131 and ZC132 were annealed to produce an overlap of 12 base pairs (Section 1). Oligomers ZC133 and ZC134 were similarly annealed (Section 2). The oligomers were mixed in Pol I buffer (Bethesda Research Labs), heated to 65° C. for five minutes, and slowly cooled to room temperature for four hours to anneal. Ten units of DNA polymerase I were added and the reaction proceeded for two hours at room temperature. The mixtures were electrophoresed on an 8% polyacrylamide-urea sequencing gel at 1,000 volts for 2½ hours in order to size fractionate the reaction products. The correct size fragments (those in which the polymerase reaction went to completion) were cut from the gel and extracted.

After annealing, Section 1 was cut with Bam HI and Nar I and cloned into Bam HI+ Nar I-cut pUC8 (Vieira and Messing, *Gene* 19: 259-268, 1982; and Messing, *Meth. in Enzymology* 101: 20-77, 1983). Section 2 was reannealed and cut with Nar I and Bgl II and cloned into Bam HI+ Nar I- cut pUC8. Colonies were screened with the appropriate labeled oligonucleotides. Plasmids identified as positive by colony hybridization were sequenced to verify that the correct sequence had been cloned.

Section 1 was then purified from a Bam HI+ Nar I double digest of the appropriate pUC clone. Section 2 was purified from a Nar I+ Xho II digest. The two fragments were joined at the Nar I site and cloned into Bam HI-cut pUC8.

The t-PA sequence of pDR1296 was then joined to the synthesized pre-pro sequence in the following manner (FIG. 2). Plasmid pIC19R (Marsh et al., *Gene* 32: 481-486, 1984) was digested with Sma I and Hind III. The ori region of SV40 from map position 270 (Pvu II) to position 5171 (Hind III) was then ligated to the linearized pIC19R to produce plasmid Zem67. This plasmid was then cleaved with Bgl II, and the terminator region from the human growth hormone gene (De Noto et al., *Nuc. Acids Res.* 9: 3719-3730, 1981) was inserted as a Bgl II-Bam HI fragment to produce plasmid Zem86. The synthesized t-PA pre-pro sequence was removed from the pUC8 vector by digestion with Bam HI and Xho II. This fragment was inserted into Bgl II-digested Zem86 to produce plasmid Zem88. Plasmid pDR1296 was digested with Bgl II and Bam HI and the t-PA cDNA fragment was isolated and inserted into Bgl II-cut Zem88. The resultant plasmid was designated "Zem94."

The vector Zem99, comprising the MT-1 promoter, complete t-PA coding sequence, and the hGH terminator, was then assembled in the following manner (FIG. 2). A Kpn I-Bam HI fragment comprising the MT-1 promoter was isolated from MThGH111 (Palmiter et al., *Science* 222: 809-814, 1983) and inserted into pUC18 to construct Zem93. Plasmid MThGH112 (Palmiter et al., ibid.) was digested with Bgl II and religated to eliminate the hGH coding sequence. The MT-1 promoter and hGH terminator were then isolated as an Eco RI fragment and inserted into pUC13 to construct Zem4. Zem93 was then linearized by digestion with Bam HI and Sal I. Zem4 was digested with Bgl II and Sal I, and the hGH terminator was purified. The t-PA pre-pro sequence was removed from the pUC8 vector as a Bam HI-Xho II fragment. The three DNA fragments were then joined, and a plasmid having the structure of Zem97 (FIG. 2) was selected. Zem97 was cut with Bgl II and-the Xho II t-PA fragment from Zem94 was inserted. The resultant vector is Zem99.

EXAMPLE 2

Replacement of Cys (83)

The t-PA coding sequence in Zem99 was mutagenized to encode a serine at position 83 (amino acid numbers refer to the sequence shown in FIG. 1). Zem99 was digested with Bam HI, and a 2.4 kb fragment comprising the t-PA coding sequence and the hGH terminator was isolated. This fragment was joined to Bam HI-digested M13mp18 (obtained from Pharmacia), and the resultant recombinant phage was used to transfect *E. coli* JM103. A phage clone having the desired insertion was designated "M13mp18/Bam-Zem99."

For site-specific mutagenesis, an oligonucleotide (sequence 5' CT GGT ATC GAT TTC ACA GCT CTT CCC AGC A 3') was synthesized and used as a mutagenic primer. The oligonucleotide was annealed to single-stranded M13mp18/Bam-Zem 99. Mutagenesis was carried out according to standard procedures and single-stranded DNA was isolated for sequencing. The replicative form of the mutagenized phage, designated "M13-9100RF," was digested with Bgl II and Hind III. A 2.3 kb fragment containing the t-PA sequence was recovered and joined to Zem99, which had been digested with Bgl II and Hind III (FIG. 3), and the DNA was used to transform *E. coli* TB1. A plasmid having the desired sequence alteration was recovered and designated "Zem99-9100." The mutated t-PA sequence of Zem99-9100 and the encoded amino acid sequence are shown in FIG. 4.

Plasmids Zem99-9100 and pSV2-dhfr (Subramani et al., ibid.) were used to transfect tk⁻BHK cells by the method of Loyter (*Proc. Natl. Acad. Sci. USA* 79: 422, 1982). Transformants were subjected to cloning by the limiting dilution method. The mutant protein, designated "9100," was purified from the cell culture media by affinity purification.

An *E. coli* TB1 transformant containing plasmid Zem99-9100 has been deposited with the Fermentation Research Institute, Agency of Industrial Science and Technology, Ministry of International Trade and Industry, Japan (FRI), under Accession No. FERM P-9269.

EXAMPLE 3

Replacement of Cys (84)

Figure 3:
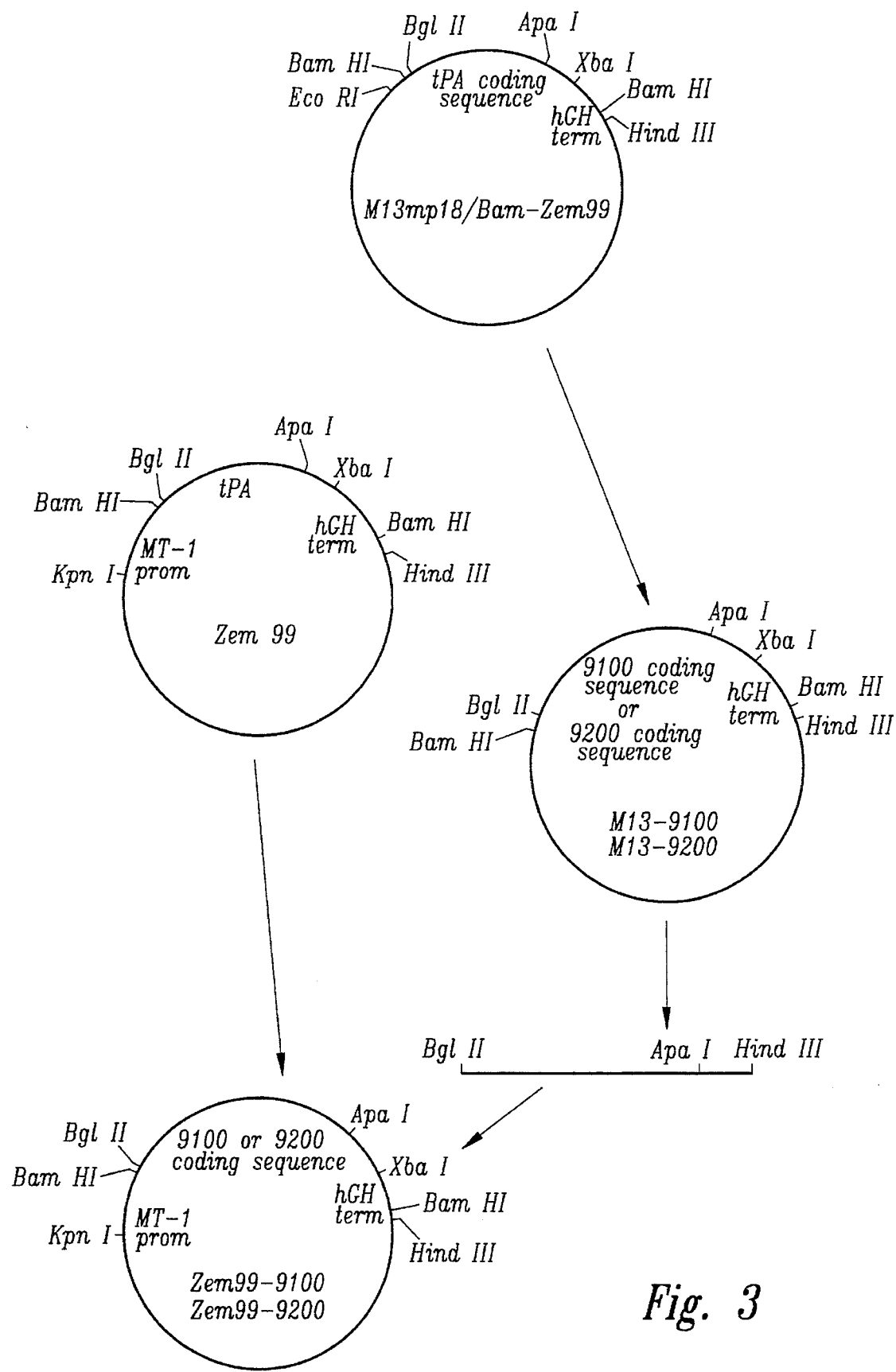
FIG. 3 illustrates the construction of the vectors Zem99-9100 and Zem99-9200.

The t-PA DNA sequence was mutagenized to encode serine at amino acid 84 by means of site-specific mutagenesis using the oligonucleotide 5' CCT GGT ATC GAT TTC ACT GCA CTT CCC 3'. The oligonucleotide was annealed to M13mp18/Bam-Zem99 and mutagenesis was carried out using standard procedures. Single-stranded mutagenized phage were sequenced and a clone having the desired sequence alternation was selected. Replicative form DNA was prepared (designated "M13-9200RF") and digested with Bgl II and Hind III. The 2.3 kb t-PA fragment was isolated and joined to the Bgl II+Hind III-cut Zem99. The resultant vector was designated "Zem99-9200" (FIG. 3). The altered t-PA coding sequence of Zem99-9200 and the encoded amino acid sequence are shown in FIG. 5.

Zem99-9200 and pSV2-dhfr were used to co-transfect tk⁻BHK cells by the method of Loyter (ibid). Transformants were subjected to cloning by the limiting dilution method. The mutant protein (9200) was purified by affinity purification.

An *E. coli* RR1 transformant containing plasmid Zem99-9200 has been deposited with FRI under Accession No. FERM P-9274.

EXAMPLE 4

Substitution for Cys in t-PA Analogs with Altered Activation Sites

Mutant DNA sequences encoding t-PA analogs either resistant to cleavage by plasmin, retaining fibrin specificity in the two-chain form, or cleavable by thrombin, were constructed by mutagenizing the native sequence to encode a glycine at position 275, a proline at position 276, or a proline at position 274.

Site-specific mutagenesis was performed on a 472 bp Eco RI fragment comprising the t-PA sequence from bp 802 to bp 1274 (see FIG. 1), which was cloned into the Eco RI site of M13mp18 (replicative form). Anti-sense strand DNA was isolated from the recombinant phage and was annealed to one of the mutagenic oligonucleotide primers ZC620 (5' CAG CCT CAG CCT CGC ATC AA 3'); ZC797 (5' CCT CAG TTC GGC ATC AAA 3'); or ZC928 (5' CAG TTT CGC CCC AAA GGA GG 3'). Twenty pmoles of phosphorylated mutagenic primer and 20 pmoles of second (universal) primer were combined with one pmole of single-stranded template DNA in 10 μl of 20 mM Tris, pH 7.5, 10 mM MgCl$_2$, 50 mM NaCl, 1 mM DTT, and the mixture was incubated at 65° C. for 10 minutes, then 5 minutes at room temperature, and placed on ice. Ten μl of 20 mM Tris, pH 7.5, 10 mM MgCl$_2$, 2 mM ATP, 10 mM DTT containing 1 mM dNTPs, 2.5 units Klenow polymerase, and 3.5 units DNA ligase was added to the annealed DNA, and the mixture was incubated 3 hours at 15° C. The DNA was then transfected into competent *E. coli* JM101 and the cells were plated on YT agar and incubated at 37° C. The DNA was then transferred to nitrocellulose and prehybridized at the Tm-4° C. of the mutagenic primer for 1 hour in 6x SSC, 10X Denhardt's, and hybridized to 32P-labeled mutagenic primer at Tm-4° C. in the same solution. After three washes at Tm-4° C., filters were exposed to X-ray film overnight. Additional wash steps were performed at 5° C. higher increments as necessary to identify mutant plaques. The mutated DNA was sequenced by the dideoxy method.

Figure 6:
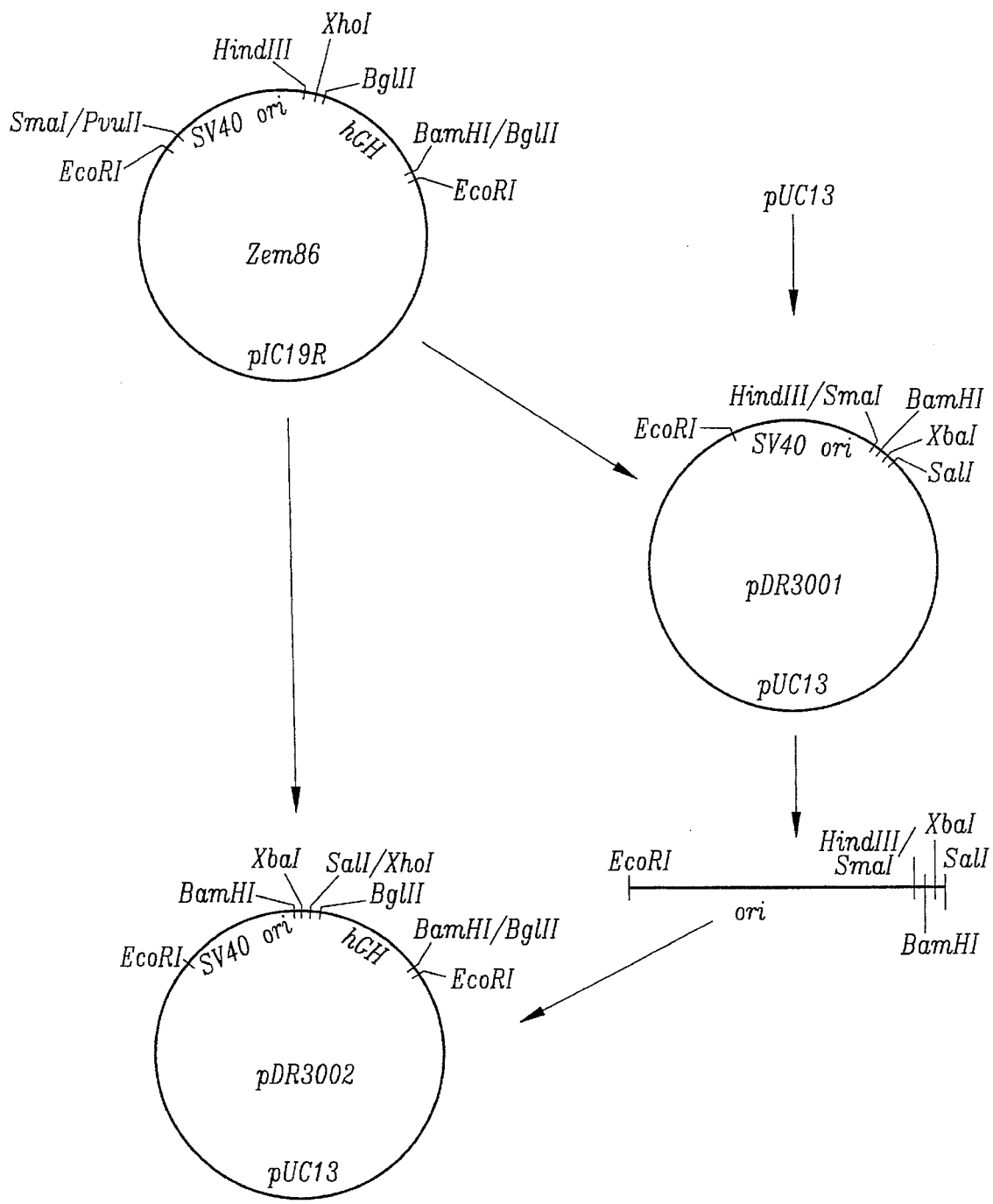
FIG. 6 illustrates the construction of plasmid pDR3002.
Figure 7:
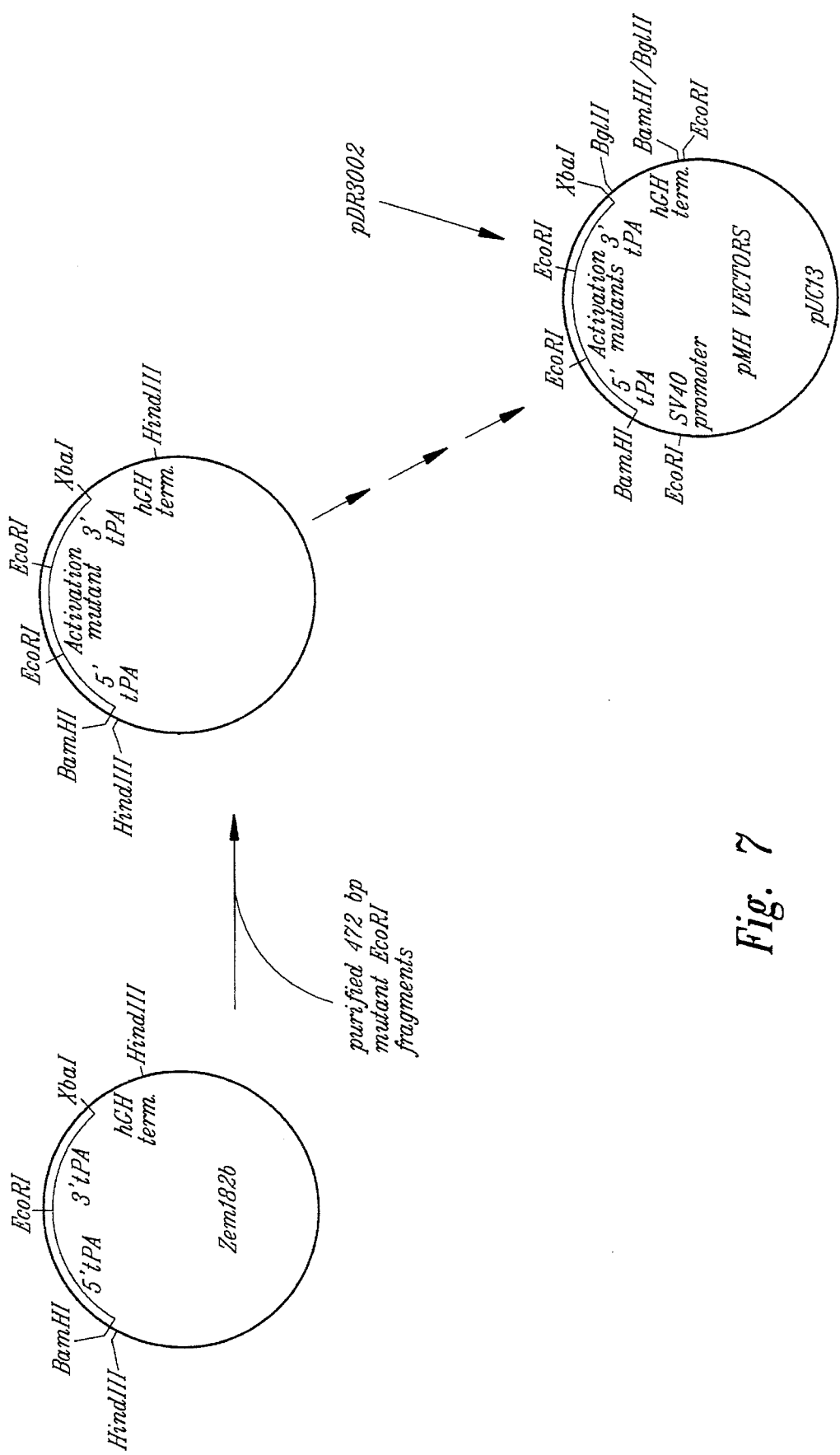
FIG. 7 illustrates the construction of plasmids pMH10, pMH13 and pMH17.

The altered sequences were then joined to the remainder of the t-PA coding sequence and the reconstructed sequences were inserted into pDR3002 (FIGS. 6 and 7). RF DNA was prepared from the mutagenized phage and the mutant DNA sequences were purified as Eco RI fragments. Plasmid Zem182b was digested with Eco RI, the vector sequences containing the 5' and 3' portions of the t-PA coding sequence were treated with calf alkaline phosphatase, and the modified t-PA sequences were inserted. The resultant plasmids were digested with Bam HI and Xba I, and the mutant t-PA fragments were inserted into Bam HI, Xba I–Cut pDR3002 to construct pMH10 (Phe (274) to Pro), pMH13 (Arg (275) to Gly), and pMH17 (Ile (276) to Pro).

Figure 8:
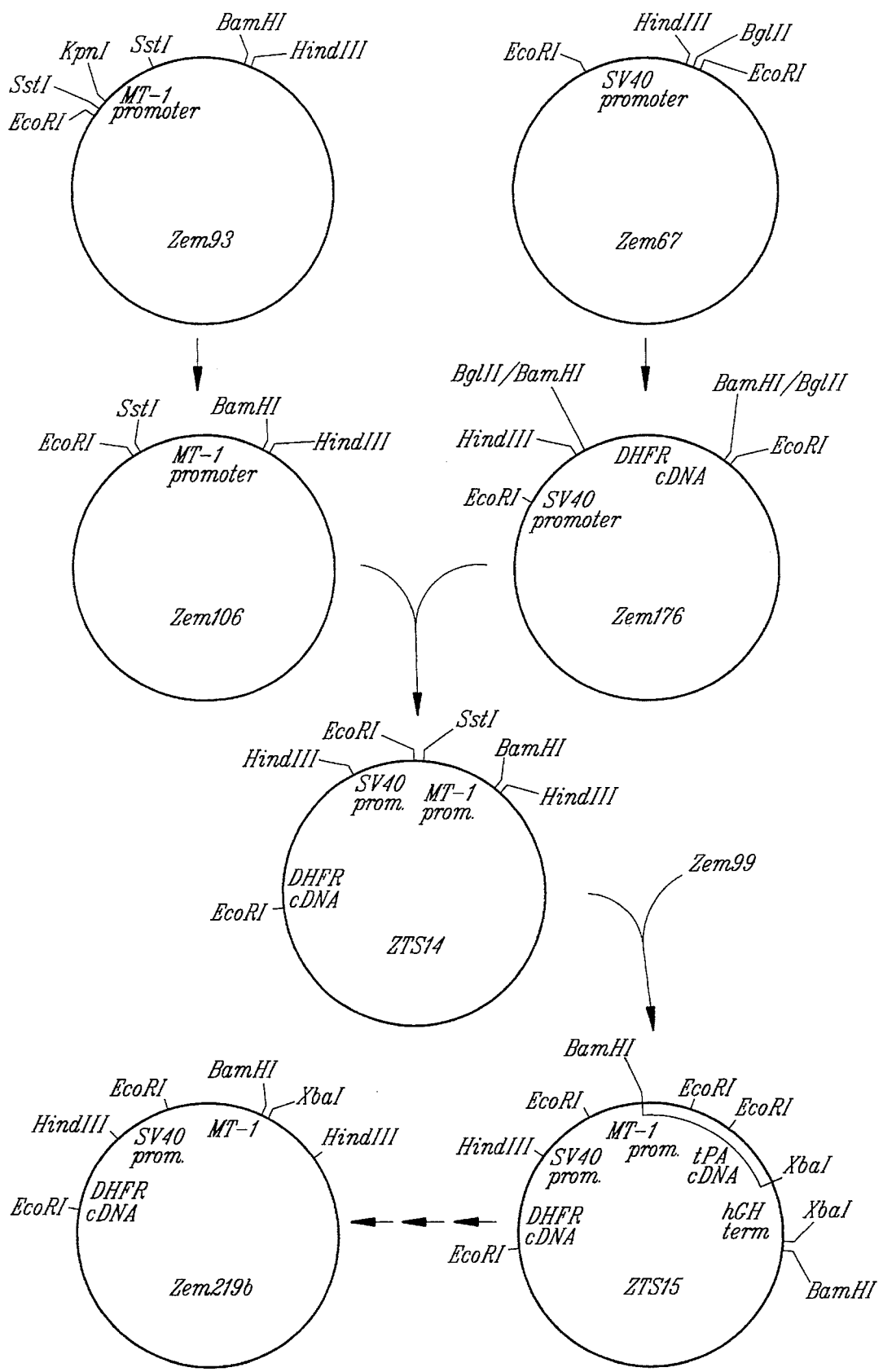
FIG. 8 illustrates the construction of the plasmid Zem219b.
Figure 9:
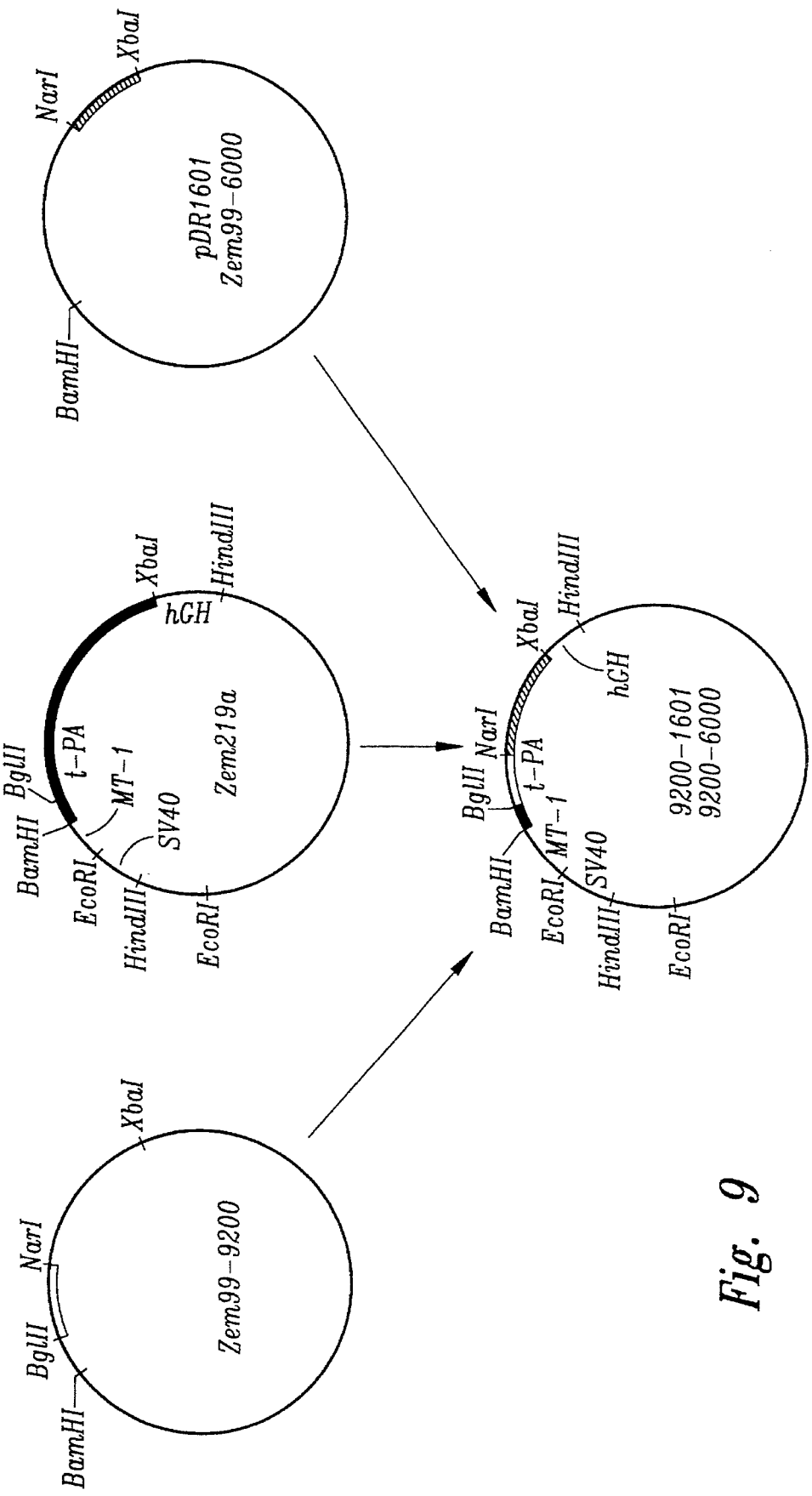
FIG. 9 illustrates the construction of the expression vectors 9200-1601 and 9200-6000.
Figure 11:
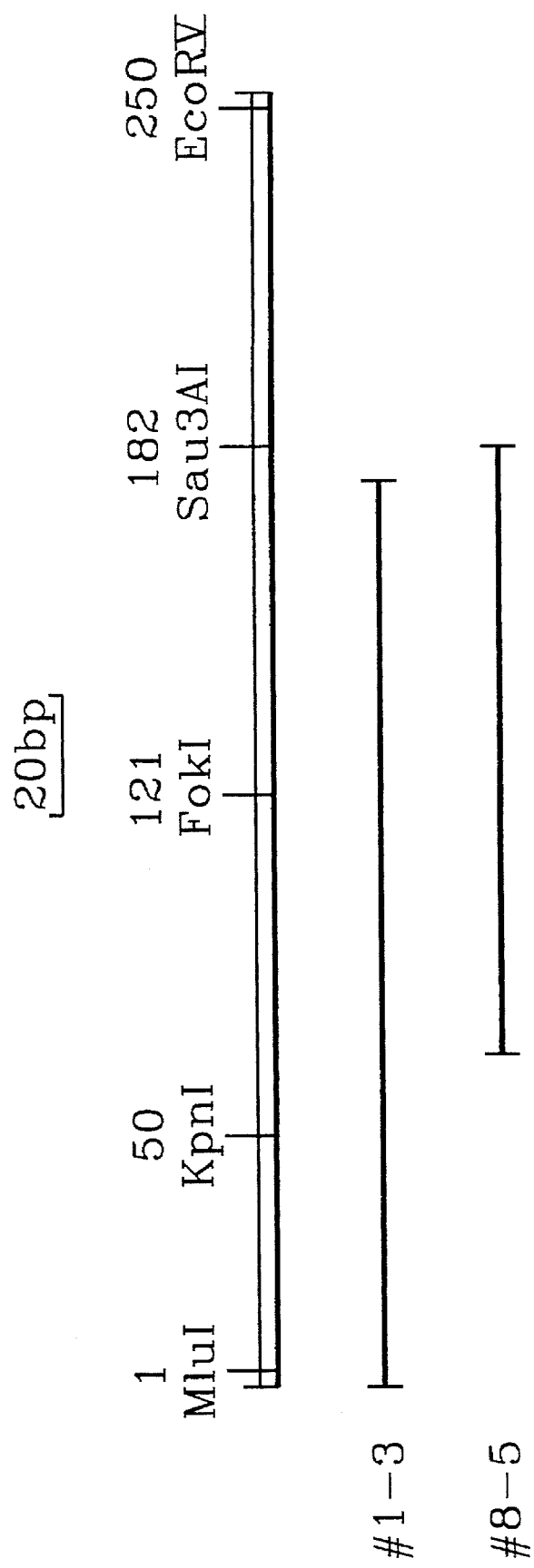
FIG. 11 shows partial restriction maps of clones #1-3 and #8-5, which encode portions of the plasminogen K1 domain.
Figure 12:
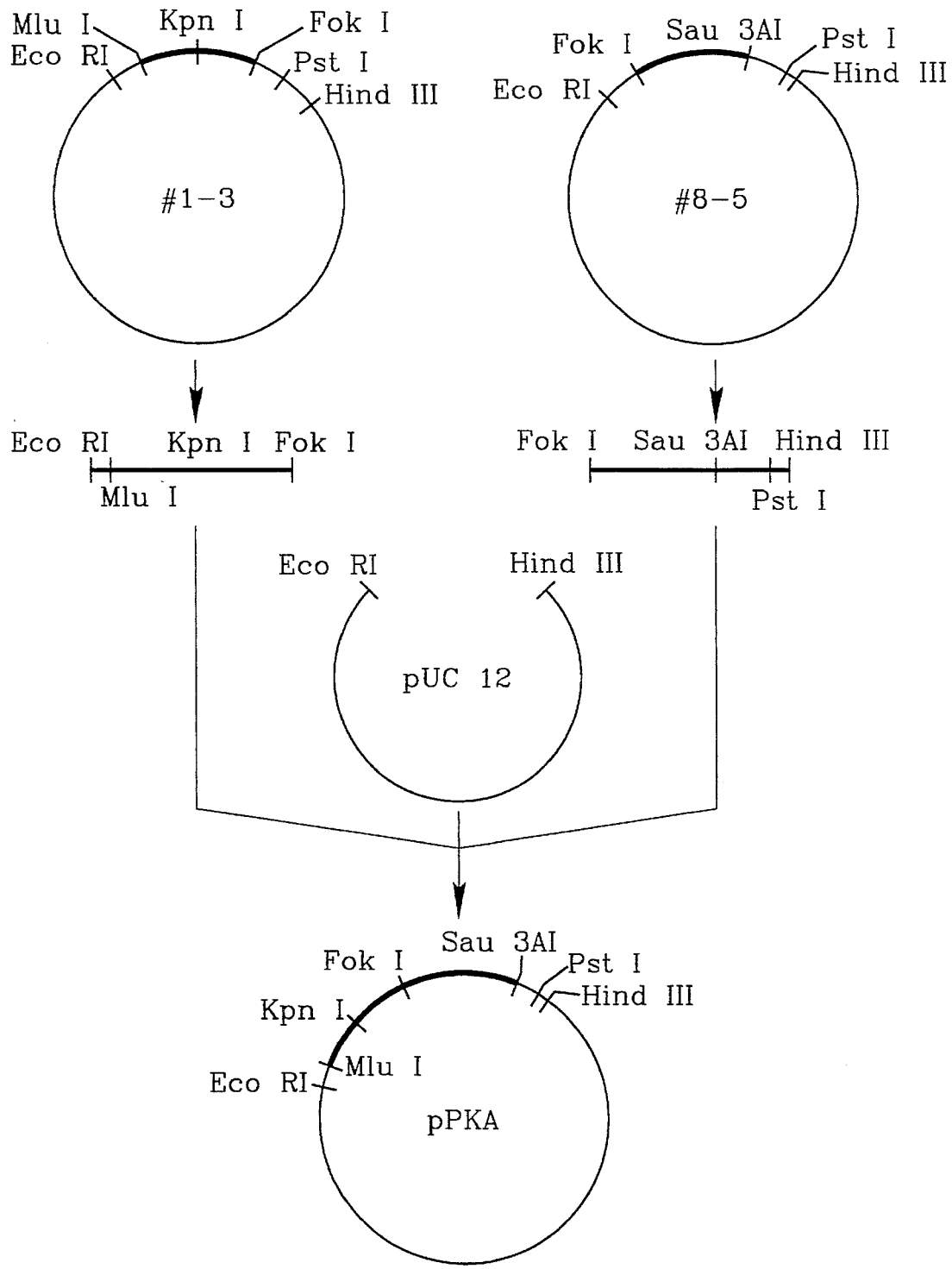
FIG. 12 illustrates the construction of plasmid pPKA.

Plasmid pSV2-DHFR (Subramani et al., ibid.) was digested with Cfo I, and the fragment containing the DHFR cDNA and the 3' attached SV40 sequences was isolated, repaired, and ligated to Bam HI linkers. After digestion with Bam HI, an approximately 800 bp fragment containing the entire cDNA and the SV40 terminator region was purified and ligated to Bam HI-digested pUC8. Zem67 (Example 1) was digested with Bgl II and ligated with the Bam HI DHFR-SV40 fragment to generate plasmid Zem176. Plasmid Zem93 was digested with Sst I and re-ligated to generate plasmid Zem106, in which approximately 600 bp of sequence 5' to the MT-1 promoter were eliminated. Plasmid Zem106 was digested with Eco RI and ligated to the Eco RI fragment containing the DHFR gene from plasmid Zem176. The resulting plasmid was designated "Zts14." Plasmid Zts14 was digested with Bam HI and ligated to the Bam HI fragment from plasmid Zem99 containing the entire t-PA coding region and hGH terminator sequence. The resulting plasmid was designated "Zts15." Zts15 was partially digested with Bam HI, repaired, re-ligated, and transformed to generate plasmid Zem219, in which the 3' Bam HI site was destroyed. Plasmid Zem219 was partially digested with Xba I, repaired, re-ligated, and transformed to generate plasmid Zem219a, in which the 3' Xba I site was destroyed. Plasmid Zem219a was digested with Bam HI and Xba I, the vector sequences purified away from the t-PA cDNA sequences, and ligated with an oligomeric Bam HI-Xba I adaptor to generate the expression vector Zem219b (FIG. 8), into which mutant Bam HI-Xba I t-PA sequences were inserted.

The modified GF domain and activation site mutations are then combined in the following manner. Cys (84) mutant DNA from Zem99-9200 is isolated as a Bam HI-Sca I fragment and joined, in a three-part ligation, to Bam HI, Xba I-digested Zem219b and the Sca I-Xba I fragment, encoding the modified activation site, from pMH10, pMH13 or pMH17. The resultant expression vectors, designated "9200-10, 9200-13 and 9200-17," are used to transfect tk⁻BHK cells by electropotation. High producer clones are scaled up and the portion is purified.

EXAMPLE 5

Substitution for Cys in a t-PA Analog Containing a Consensus Finger Domain

Replacement of the t-PA finger domain with a consensus finger region results in the elimination of potential proteolytic cleavage sites at Arg-27, Lys-49 and Arg-89. Eight finger replacement sequences were constructed, based on an analysis of the finger domains of fibronectin and t-PA.

The consensus finger sequences were constructed from oligonucleotides as described below, then inserted into the t-PA coding sequence. To facilitate this insertion, a Kpn I site was introduced downstream (3') of the region encoding the wild-type finger domain. Digestion of the resulting sequence with Bgl II and Kpn I resulted in the deletion of the wild-type finger domain.

A. Kpn I Site Insertion Between the Finger and Growth Factor Domains

In order to place a Kpn I site after the finger domain in t-PA, a mutagenesis was performed with oligonucteotide ZC986 (5' TTT GAC AGG TAC CGA GTG GCA 3'). DNA of a phage M13 clone containing the 5' Bam HI-Eco RI fragment of the native t-PA cDNA was prepared. 100 μl of the DNA solution was used to infect *E. coli* RZ1032 in 100 μl of YT medium supplemented with 0.1 μg/ml uridine. This culture was incubated at 37° C., with vigorous shaking, overnight. Growing the M13 in RZ1032 produces phage containing uridine which are viable in RZ1032 but not in JM101.

The cells were spun out, and the phage supernatant was used to reinfect *E. coli* RZ1032. This second passage was performed to dilute out any JM101-derived phage which contained no uracil. Again, the cells were spun out and the phage were plated on JM101 and RZ1032. Normal viability was observed on RZ1032 plates (indicating phage at $10^9$ pfu/ml), but no plaques were observed on JM101 cells. A complementary strand primed with the mutagenic oligonucleotide was then produced in vitro. The new strand, containing the mutation, contained thymidine and was therefore viable in JM101; the wild-type template was not.

Template DNA was prepared by PEG precipitation of the phage supernatant followed by phenol-chloroform extraction and ethanol precipitation. One µg of this template DNA was hybridized with 10 µg of oligonucleotide ZC986 by briefly boiling, incubating at 65° C. for 5 minutes, and then slowly bringing the temperature down to 4° C. before adding 10 µl 0.2 M HEPES pH 7.8, 2 µl 100 mM DTT, 1 µl 1 M $MgCl_2$, 20 µl 2.5 mM each dNTP, 10 µl 10 mM ATP, 1 µl 2.5 U/µl Klenow, and 2 µl 1 U/µl $T_4$ DNA ligase, final volume adjusted to 100 µl with $H_2O$. After extension at 37° C. for 2 hours, the DNA was transfected into competent JM101 cells. A control extension (minus oligonucleotide) was performed to compare the amount of background produced by extension by priming on contaminating RNA or DNA species. The transfection produced zero plaques with unmutagenized template, 150 on control extension (minus oligonucleotide) and 300 with mutagenized template.

The plates were screened by hybridizing a plaque lift with 32P-labeled mutagenic oligonucleotide and washing in 3 M TMAC1 (Wood et al., *Proc. Natl. Acad. Sci. USA* 82: 1585–1588, 1985) at Tm-5° C. for 30 minutes and also by sequencing randomly picked plaques. One positive clone was obtained.

B. Production of Finger Replacement Domains

The consensus finger region replacements shown in Table 1 and FIG. 20 were constructed.

TABLE 1

| Finger | Encoded Amino Acid Sequence | Oligonucleotides* |
|---|---|---|
| t-PA wild-type: | CRDEKTQMIYQQHQSWLRPVLR-SNRVEYCWC--N-SGRAQC | |
| Consensus 1: | CFD--NGKSYKIGETWERPYE--GFMLS-CTCLGNGRGEFRC | (ABC) |
| Consensus 2: | CHDEKTGSSYKIGEQWERPYL-SGNRLE-CTCLGNGSGRWQC | (DEF) |
| Consensus 3: | CFD--NGKSYKIGETWERPYE--GFMLS-CTCLGNGSGRWQC | (ABF) |
| Consensus 4: | CFD--NGKSYKIGEQWERPYL-SGNRLE-CTCLGNGRGEFRC | (AEC) |
| Consensus 5: | CFD--NGKSYKIGEQWERPYL-SGNRLE-CTCLGNGSGRWQC | (AEF) |
| Consensus 6: | CHDEKTGSSYKIGETWERPYE--GFMLS-CTCLGNGSGRWQC | (DBF) |
| Consensus 7: | CHDEKTGSSYKIGEQWERPYL-SGNRLE-CTCLGNGRGEFRC | (DEC) |
| Consensus 8: | CHDEKTGSSYKIGETWERPYE--GFMLS-CTCLGNGRGEFRC | (DBC) |

*A = ZC1116/1117
B = ZC1118/1119
C = ZC1120/1121
D = ZC1122/1123
E = ZC1124/1125
F = ZC1126/1127

TABLE 2

```
ZC1116
GAT CTT ATC AAG TCA TAT GTT TTG ATA ATG GAA AAT CTT ATA A
ZC1117
CTC CAA TTT TAT AAG ATT TTC CAT TAT CAA AAC ATA TGA CTT GAT
AA
ZC1118
AAT TGG AGA AAC ATG GGA ACG GCC GTA TGA AGG ATT TAT GCT TTC
T
ZC1119
CAT GTA CAA GAA AGC ATA AAT CCT TCA TAC GGC CGT TCC CAT GTT
T
ZC1120
TGT ACA TGC CTA GGA AAT GGC CGC GGA GAA TTT AGA TGT CAT TCG
GTA C
ZC1121
CGA ATG ACA TCT AAA TTC TCC GCG GCC ATT TCC TAG G
ZC1122
GAT CTT ATC AAG TCA TAT GTC ATG ATG AAA AAA CAG GCT CGA GTT
ATA A
ZC1123
CTC CAA TTT TAT AAC TCG AGC CTG TTT TTT CAT CAT GAC ATA TGA
CTT GAT AA
ZC1124
AAT TGG AGA ACA ATG GGA ACG GCC GTA TCT TTC TGG AAA TCG ATT
AGA A
ZC1125
CAT GTA CAT TCT AAT CGA TTT CCA GAA AGA TAC GGC CGT TCC CAT
TGT T
ZC1126
TGT ACA TGC CTA GGA AAT GGT TCC GGA AGA TGG CAA TGT CAT TCG
GTA C
ZC1127
CGA ATG ACA TTG CCA TCT TCC GGA ACC ATT TCC TAG G
```

The eight consensus sequences were generated from the indicated oligonucleotides. The oligonucleotides (Table 2) were produced using an Applied Biosystems Model 380A DNA synthesizer. First, the twelve oligonucleotides were kinased and simultaneously labeled to a low specific activity with γ32p ATP by incubating each with polynucleotide kinase at 37° C. for ½ hour. Then the indicated eight combinations (ABC, DEF, ABF, AEC, AEF, DBF, DEC and DBC) were produced by mixing the appropriate oligonucleotides, adding DNA ligase, and incubating at 37° C. for 1 hour. The products of this reaction were sorted out on a 6% polyacrylamide- 8M urea sequencing gel. The bands corresponding to the DNA coding for full-length finger domains were cut out, and the DNA was eluted in 2.5M ammonium acetate. The DNA was ethanol-precipitated and resuspended in water to a concentration of 1 pmole/μl.

RF DNA was prepared from the positive clone described in Example 5A, and the Bam HI to Eco RI t-PA fragment was purified. Plasmid Zem219a (described in Example 4) was digested with Xba I and then partially digested with Eco RI. The 1010 bp fragment, containing the 3' t-PA coding region, was purified. Plasmid Zem219b (described in Example 4) was digested with Bam HI and Xba I and ligated to the 5' t-PA fragment (Bam HI-Eco RI) and the 1010 bp Eco RI-Xba I fragment. The resulting vector, designated "Zem238," contains a Kpn I site after the finger domain. Zem238 was digested with Bgl II and Kpn I, gel-purified to remove the wild-type finger domain, and ligated with each of the eight consensus sequences to generate expression vectors 238-Fcon 1 to 238-Fcon 8.

C. Combination of Cys (84) Substitution with Consensus Finger

Template DNA from M13-9200 (Example 3) is annealed to oligonucleotide primer ZC986, as described in Example 5A. A correctly mutated clone with a Kpn I site inserted at the 3' end of the finger domain is identified and sequenced. RF DNA from this clone is digested with Kpn I and Xba I, and the Cys (84) mutant DNA is ligated to vector DNA from Kpn I, Xba I-digested plasmids 238-Fcon 1 to 238-Fcon 8. The resultant vectors, designated "9200-Fcon 1" to "9200-Fcon 8," are transfected into tk⁻BHK cells and the mutant proteins are purified and characterized.

EXAMPLE 6

Modification of Carbohydrate Attachment Sites in Cys-Substituted t-PA Analogs

Tissue plasminogen activator contains four potential glycosylation sites (amino acid sequence Asn-X-Ser/Thr. According to Pohl et al. (Biochemistry 23: 3701–3707, 1984), three of these sites (Asn-117, -184 and -448) are glycosylated in t-PA obtained from Bowes melanoma cells. By altering the Asn residues at the glycosylation sites to other amino acid residues, the glycosylation is blocked. It is particularly preferred that the Asn residues be changed to Gln residues. Alterations in the DNA sequence encoding t-PA are made by site-specific mutagenesis. Nucleotide changes may be made singly or in combination to alter one or more of the glycosylation sites. Additionally, mutated sequences may be combined with DNA fragments comprising other deletions, insertions or substitutions of the t-PA coding sequence in order to generate new proteins comprising several mutations in combination.

Site-specific mutagenesis was carried out on single-stranded M13 phage templates using mutagenic primers ZC294, ZC295 and ZC297 (see Table 3) to produce the alterations at Asn-117, -184 and -448, respectively. DNA sequences encoding mutant t-PAs were then constructed comprising single, double or triple mutations by replacing the t-PA coding sequences in pDR1296. The following plasmids were constructed: (1) pDR1601, comprising the mutation at Asn-117; (2) pDR1602, comprising the mutation at Ash-184; (3) pDR1603, comprising the mutation at Ash-448; (4) pDR1604, comprising the mutations at Asn-117 and -448; (5) pDR1605, comprising the mutations at Asn-184 and -448; and (6) pDR1606, comprising the three mutations.

TABLE 3

| Primer | Sequence |
| --- | --- |
| ZC294 | 5'ACC AAC TGG CAA TCT TCT GCG TTG GCC3' |
| ZC295 | 5'TGC TAC TTT GGT CAA GGG TCA GCC3' |
| ZC297 | 5'CAA CAT TTA TTG CAA AGA ACA GTC3' |

In an additional mutagenesis, an oligonucleotide primer (5' ACG GTA GGC TGT CCC ATT GCT AAA GTA GCA 3') was prepared in order to replace Gly (183) and Set (186) with Sr and Thr, respectively. These mutations result in more uniform glycosylation of the K2 domain. Site-specific mutagenesis was performed according to the one-primer method, using the template M13mp18/Bam-Zem99 (Example 2). Single-stranded mutated phage DNA was prepared and sequenced. A clone having the desired sequence alteration was designated "M13-6000."

RF DNA from M13-6000 was isolated, digested with Bgl II and Apa I, and a fragment of approximately 1.4 kb was isolated. This fragment was joined to Bgl II, Apa I-digested Zem99 to produce the vector Zem99-6000. *E. coli* RR1 transformed with Zem99-6000 has been deposited with the Fermentation Research Institute under Accession No. FERM p-9126.

Cys (84) mutant DNA from plasmid Zem99-9200 is digested with Bgl II and Nar I. The mutant DNA sequences are isolated from pDR1601 and Zem99-6000 as Nar I-Xba I fragments. Plasmid 9200-1601 is generated by ligation of the Bgl II-Nar I fragment from Zem99-9200, the Nar I-Xba I fragment from pDR1601 and the Bgl II-Xba I (vector) fragment of Zem219a. Plasmid 9200-6000 is generated by ligation of the Bgl II-Nar I fragment from Zem99-9200, the Nar I-Xba I fragment from Zem99-6000, and the Zem219a vector fragment. These plasmids are used to transfect tk⁻BHK cells by electropotation. The mutant proteins are purified and characterized.

EXAMPLE 7

Combination of Cys Substitution with Kringle Domain Replacement

A. Asp (96) Plasminogen Kringle

Plasmid pK1 comprises a coding sequence for the K1 domain of plasminogen, the sequence of which is shown in FIG. 10. It was constructed from a series of eleven oligonucleotides designated "PK1-1, PK1-2, PK1-3, —PK1-12," the sequences of which are shown in Table 4.

TABLE 4

| Oligonucleotide | Sequence |
|---|---|
| PK1-1 | 5'GAT CCA CGC GTG CCA CGT GCA AGA CCG GTG ATG GTA AAA ACT ACC GAG GTA CCA TGT CCA AGA CC3' |
| PK1-2 | 5'AAA AAC GGT ATT ACA TGT CAG AAA TGG TCA TCT ACT AGT CCA CAC CGG CCG CGG TTT TCT3' |
| PK1-3 | 5'CCA GCT ACC CAT CCA TCT GAA GGC CTG GAA GAG AAT TAC TGT AGG AAT CCA GAT AAC GAT3' |
| PK1-4 | 5'CCT CAG GGT CCC TGG TGT TAC ACC ACA GAC CCC GAG AAG AGG TAC GAC TAC TGC GAT ATC GCA TG3' |
| PK1-5 | 5'CCG TTT TTG GTC TTG G3' |
| PK1-6 | 5'GTA GCT GGA GAA AAC CG3' |
| PK1-7 | 5'CCC TGA GGA TCG TTA TC3' |
| PK1-9 | 5'CGA TAT CGC AGT AGT CGT ACC TCT TCT C3' |
| PK1-10 | 5'GAT CCT CAG GGT CCC TGG TGT TAC ACC ACA3' |
| PK1-11 | 5'GAC CCC GAG AAG AGG TAC GAC TAC TGC GAT ATC GCA TG3' |
| PK1-12 | 5'GGG GTC TGT GGT GTA ACA CCA GGG ACC CTG AG3' |

The coding sequence for nucleotides 1 through 182 of the plasminogen K1 domain was constructed from oligonucleotides PK1-1 through PK1-7 in the following manner. 100 pmole each of the oligonucleotides PK1-1, PK1-2, PK1-3 and PK1-4 were phosphorylated at their 5' termini. The phosphorylated oligonucleotides were mixed with 100 pmole each of PK1-5, PK1-6, and PK1-7. The mixture was precipitated with ethanol, and the precipitate was resuspended in $H_2O$ and heated for 3 minutes at 90° C. The solution was then left to stand at room temperature for ten minutes, then placed on ice. To the chilled mixture was added 10 μl of 660 mM Tris HCl, pH 7.6, containing 6.6 mM $MgCl_2$, 10 μl of 0.1M dithiothreitol, 10 μl of 5 mM ATP, and 1000 units of $T_4$ DNA ligase. The mixture was incubated 15 hours at 14° C. Ethanol was added and the precipitate was resuspended in 20 μl of TE buffer (10 mM Tris-HCl, 1 mM EDTA, pH 8.0)), followed by the ,addition of an equal volume of alkali loading buffer (20 mM NaCl, 2 mM EDTA, 80% formamide, 0.1% xylene cyanol and 0.1% bromphenol blue). The mixture was heated for three minutes at 90° C. and electrophoresed on a 6% polyacrylamide gel containing 8.4M urea for one hour at 300 volts. The gel was stained with ethidium bromide and a 250 bp band was recovered by electrophoretic transfer to DEAE-cellulose paper (Dretzen et al., *Anal. Biochem.* 112: 295–298, 1981). The recovered DNA was solubilized in 100 μl of TE buffer and the fragment was designated "PK1-n." PK1-n was C-tailed at the 3' terminus by combining 10 μl of PK1-n with 2 μl of 100 mM sodium cacodylate—25 mM HEPES, pH 7.6, 6.2 μl of 1 mM dCTP, 10 units terminal deoxynucleotidyl transferase and 5 μl of $H_2O$. The reaction mix was incubated at 37° C. for 10 minutes, then extracted with phenol:chloroform (1:1).

One μl of 3'-oligo (dG) tailed pUC9 (obtained from Pharmacia) was cleaved with Sma I. The linearized, tailed plasmid was added to the C-tailed PK1-n. The mixture was then ethanol precipitated and the DNA was resuspended in 0.5 μl of 2M KCl and 9.5 μl of TE buffer, and incubated at 65° C. for 10 minutes, then cooled to room temperature. To the cooled mixture were added 5 μl of 0.2 M Tris HCl, pH 7.5, containing 0.1M $MgCl_2$ and 0.1M dithiothreitol, 20 μl of 2.5 mM dNTPs, 10 μl of 5 mM ATP, 53 μl $H_2O$, 5 units DNA polymerase I (Klenow fragment), and 300 units $T_4$ DNA ligase (final volume of 100 μl). The mixture was incubated at 14° C. for 12 hours, then used to transfect *E. coli* JM83.

The transfected JM83 cells were probed with PK1-6 using the method of Wallace et al. (*Nuc. Acids Res.* 9: 879–894, 1981). Twenty positive clones were sequenced and two were selected: #1-3, including base pairs 1-170, and #8-5, including base pairs 68-186 (see FIG. 11).

Referring to FIG. 12, clone #1-3 was digested with Eco RI and Fok I, and a 130 bp fragment containing a Kpn I site was recovered. Similarly, clone #8-5 was digested with Fok I and Hind III, and a 90 bp fragment was recovered. The two fragments were joined to Eco RI, Hind III-digested pUCl2 and the resultant plasmid was designated "pPKA." This plasmid thus contains a DNA sequence corresponding to nucleotides 1-182 of the plasminogen K1 sequence.

The remainder of the K1 sequence was constructed using oligonucleotides PK1-9, PK1-10, PK1-11 and PK1-12. One pmole each of the oligonucleotides was phosphorylated at the 5' end, and the combined oligos were mixed with 40 μg of Bam HI, Sph I-digested M13tg130RF (obtained from Amersham). To this mixture were added 4 μl of 660 mM Tris-HCl, ph 7.6, containing 66 mM $MgCl_2$, and 22 μl of $H_2O$. The solution was heated for three minutes at 90° C. and allowed to cool to room temperature over a period of one hour. Four μl of 0.1M dithiothreitol, 4 μl of 5 mM ATP, and 300 units of $T_4$ DNA ligase were added, and the mixture was incubated for 12 hours at 14° C. The resulting phage clone, designated "M13PKB RF" (FIG. 13), contained nucleotides 183 through 250 of the plasminogen K1 sequence.

Figure 13:
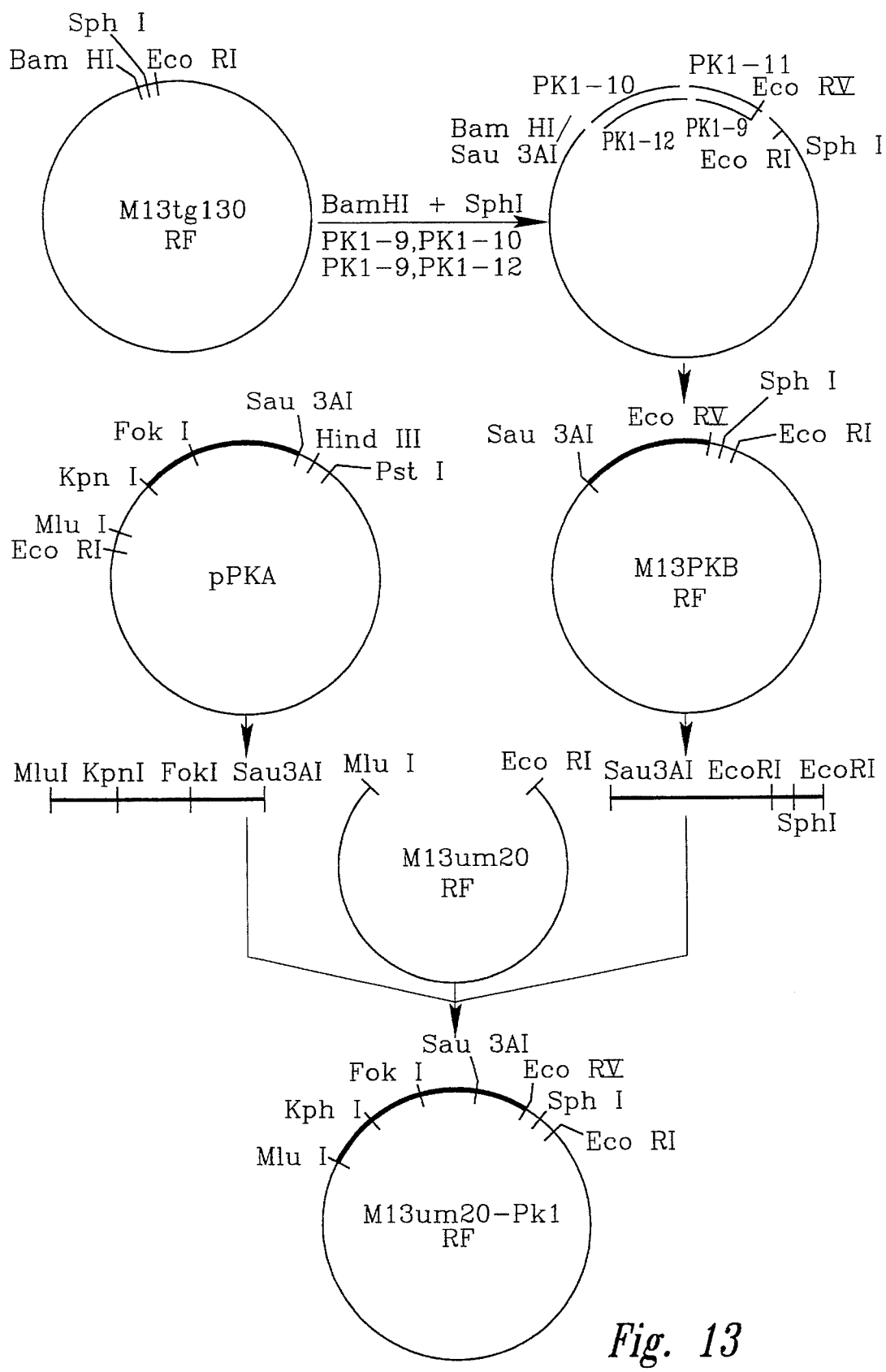
FIG. 13 illustrates the construction of a vector containing the plasminogen K1 coding sequence.

The assembly of the complete plasminogen K1 coding sequence is illustrated in FIG. 13. Plasmid pPKA was digested with Mlu I and Sau 3AI, and a 176 bp fragment was recovered. M13PKB RF was digested with Sau 3AI and Eco RI, and an 88 bp fragment was recovered. These fragments were joined to Mlu I, Eco RI-digested M13um20 RF (obtained from IBI), and the resultant plasmid was designated "M13um20-PK1."

Figure 14:
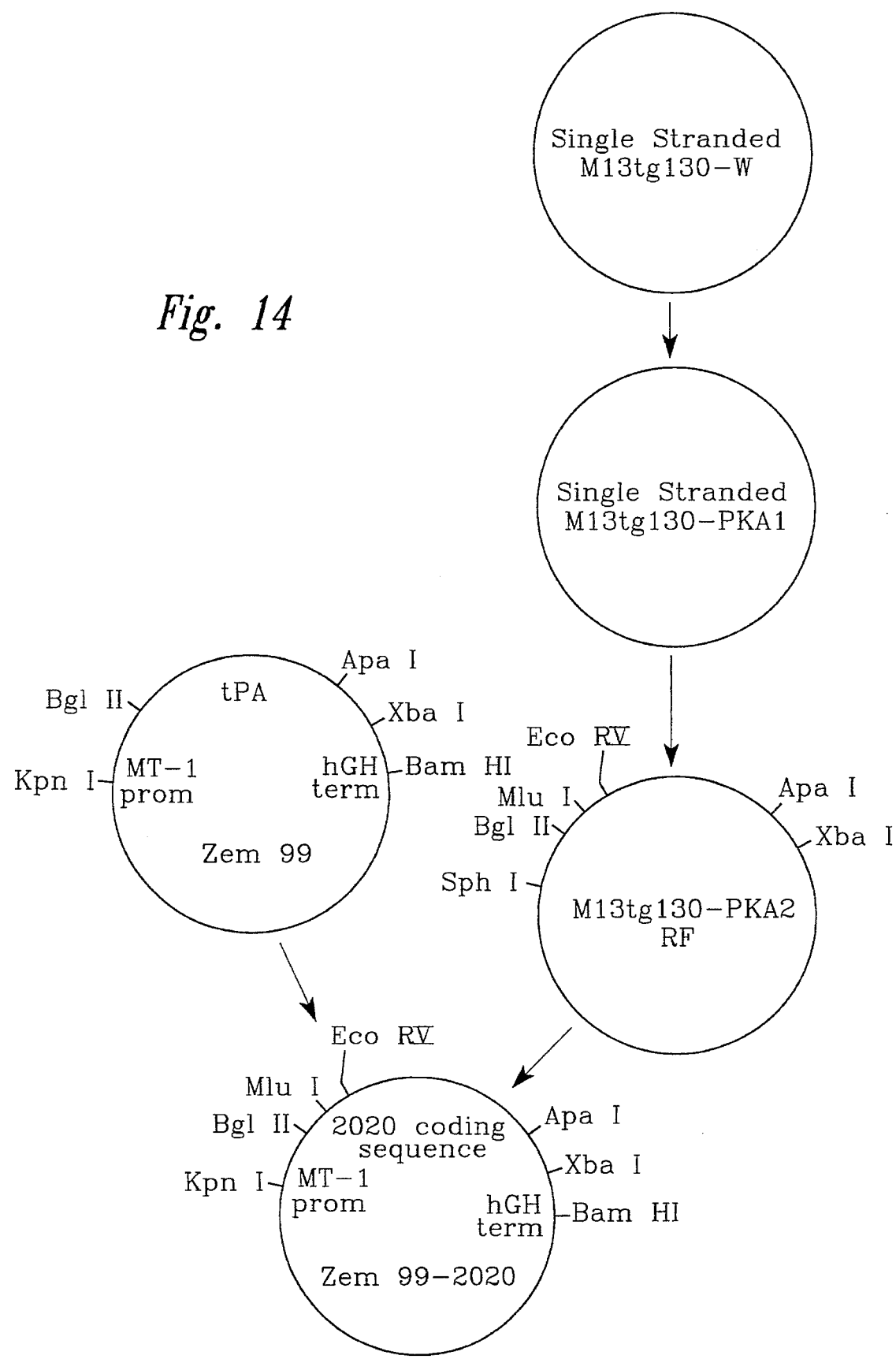
FIG. 14 illustrates the construction of plasmid Zem99-2020.
Figure 15:
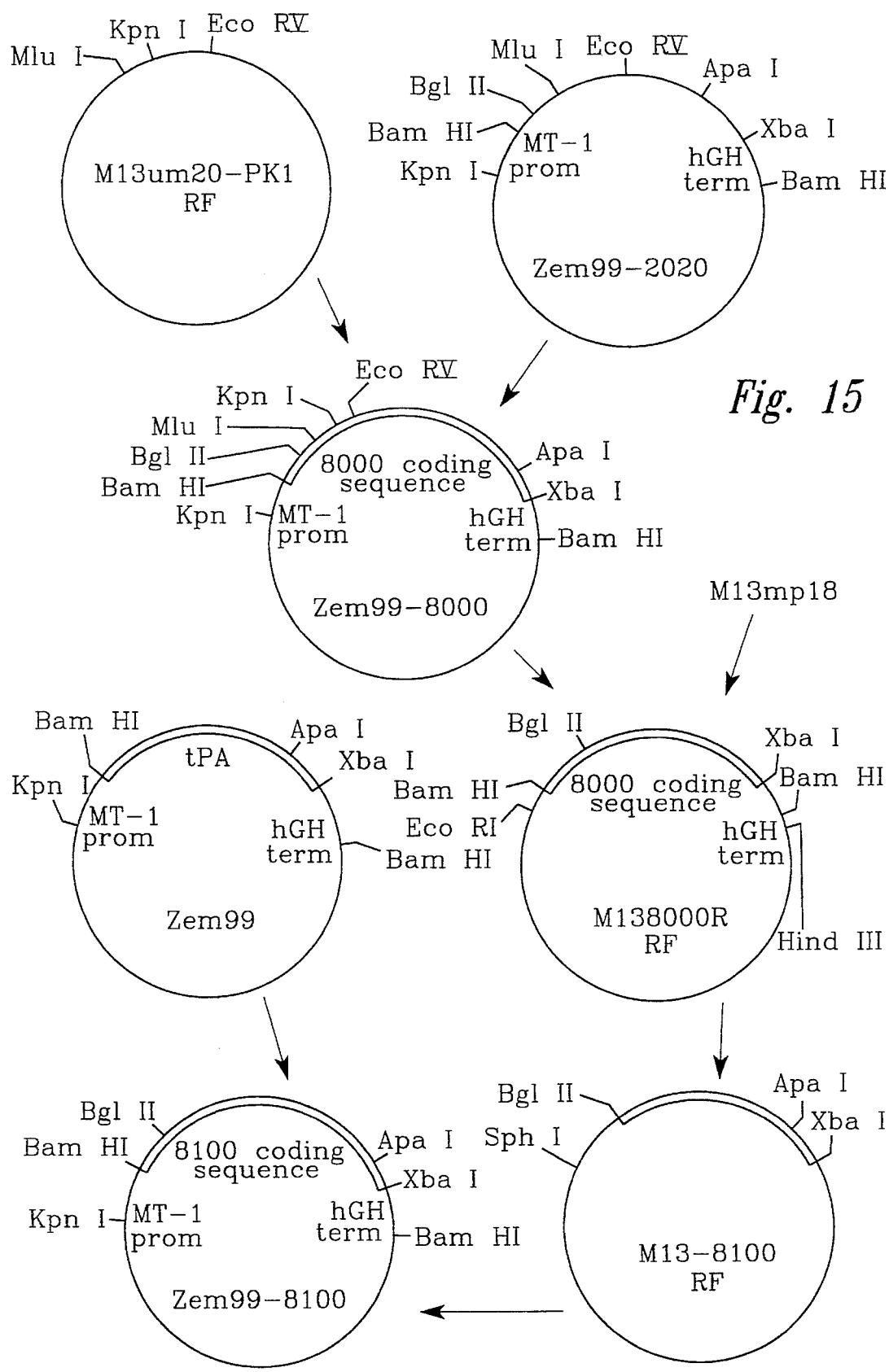
FIG. 15 illustrates the construction of the plasmids Zem99-8000 and Zem99-8100.

The PK1 coding sequence was then inserted into the t-PA cDNA as a replacement for the t-PA Kringle 1 sequence (FIGS. 14 and 15). The t-PA sequenced was first mutagenized to insert Mlu I and Eco RV sites. Plasmid pDR1496 was digested with Sph I and Xba I, and the 2.1 kb fragment comprising the alpha factor and t-PA sequences was isolated. (*S. cerevisiae* strain E8-11C transformed with pDR1496 has been deposited with American Type Culture Collection under Accession No. 20728.) This fragment was joined to Sph I, Xba I-digested M13tg130 (RF), and the resultant phage was designated "M13tg130-W." Single-stranded phage. DNA was then annealed to an oligonucleotide (5' GCA CGT GGC ACG CGT ATC TAT TTC 3') and mutagenesis was carried out according to standard procedures. The mutagenized phage was designated "M13tg130-PKA1." Single-stranded DNA of M13tg130-PKA was isolated and mutagenized by the one-primer method with an oligonucleotide having the sequence 5' CTC AGA GCA TTC CAG GAT ATC GCA GAA CTC 3'. Single-stranded DNA was prepared from the mutagenized phage and sequenced. A clone containing an Mlu I site at the 5' end and an Eco RV site at the 3' end of the Kringle 1 coding sequence was selected and designated "M13tg130-PKA2."

Replicative form DNA was prepared from M13tg130-PKA2 and was digested with Bgl II and Apa I. The fragment containing the Mlu I and Eco RV sites was recovered and joined to Bgl II, Apa I-digested Zem99, as shown in FIG. 14. The resultant plasmid was designated "Zem99-2020."

The PK1 sequence was then inserted into the t-PA cDNA. M13um20-PK1 RF was digested with Mlu I and Eco RV, and the 336 bp fragment was recovered. This fragment was joined to Mlu I, Eco RV-digested Zem99-2020 to construct Zem99-8000 (FIG. 15). The t-PA coding sequence of Zem99-8000 and the encoded amino acid sequence are shown in FIG. 16.

B. Asn (96) Plasminogen Kringle

A second plasminogen K1 sequence encoding Asn at position 96 was constructed (FIG. 15). Zem99-8000 was digested with Bam HI, and the fragment containing the Bgl II site was recovered. This fragment was joined to Bam HI cut M13mp18 to construct M13-8000R. An oligonucleotide primer (sequence 5' TTT TTA CCA TTA CCG GTC TT 3') was annealed to single-stranded M13-8000R, and mutagenesis was carried out according to routine procedures for the one-primer method. Clones were screened and sequenced, and double-stranded DNA, designated "M13-8000RF," was prepared from a positive clone. This phage was digested with Bgl II and Apa I, and the t-PA fragment was isolated and joined to Bgl II, Apa I–cut Zem99. The resultant plasmid was designated "Zem99-8100." The t-PA coding sequence present in Zem99-8100 and the encoded amino acid sequence are shown in FIG. 17.

Plasmids Zem99-8000 and Zem99-8100 have been deposited (as *E. coli* RRI transformants) with FRI under Accession Nos. FERM P-9272 and FERM P-9315, respectively.

C. Combination of Cys Replacement and K1 Substitution

Single-stranded DNA was isolated from M13-9200 and was mutagenized using the oligonucleotide 5' GCA CGT GGC ACG CGT ATC TAT TTC 3' to introduce an Mlu I site. The mutagenized phage was designated "M13-92.05PKA1." RF DNA was prepared from the mutant phage and was digested with Bgl II and Mlu I, and the 264 bp fragment was recovered. Zem99-8000 was digested with Mlu I and Apa I, and the 1126 bp fragment was recovered. These two fragments were joined to Bgl II, Apa I-digested Zem99, and the resultant plasmid was designated "Zem99-9280." This plasmid thus encodes a mutant t-PA with Set at amino acid 84 and the K1 domain of plasminogen with Asp at position 96.

A second vector, which contains a mutant t-PA sequence encoding a t-PA analog with Set at amino acid 84 and the K1 domain of plasminogen with Ash at position 96, was constructed. RF DNA from M13-92.05PKA1 was digested with Bgl II and Mlu I, and the 264 bp fragment was recovered. Zem99-8100 was digested with Mlu I and Apa I, and the 1126 bp fragment was recovered. These two fragments were joined to Bgl II, Apa I-digested Zem 99, and the resultant plasmid was designated "Zem99-9281."

EXAMPLE 8

Characterization of Proteins

Proteins 9100 and 9200 were prepared as described and tested for activity and plasma half-life using native t-PA prepared from transfected tk⁻BHK cells as a control.

t-PA analogs #9100 and #9200 were tested for clot lysis activity using native recombinant t-PA as a control. A silk thread 3 cm in length was introduced into an Atom venous catheter (4Fr 3.5 cm) and the catheter was connected to an injection syringe. Human citrated blood was prepared by mixing blood and a solution of 3.8% sodium citrate in a 9:1 ratio. The citrated blood (0.5 ml) was combined with $^{125}I$-fibrinogen (25 μCi in 50 μl of physiological saline solution), 50 μl of 0.25M $CaCl_2$ and thrombin (5 U/10 μl of solution). 16 μl of the resulting solution was injected into the catheter and the catheter was allowed to stand at room temperature for 60 minutes. The silk thread was then removed from the catheter and washed with a physiological saline solution. The radioactivity bound to the thread (the initial fibrin thrombus value) was determined. The thread was then introduced into a carotid arteriovein (A-V) shunt on a male Sprague-Dawley rat weighing between 200 and 300 grams. One ml samples of the protein in a saline solution containing 50 units heparin per ml were injected into the femoral vein of the animal. After two hours, the silk thread was removed from the shunt and the radioactivity (residual fibrin thrombus value) was determined. The residual thrombus ratio was determined according to the equation:

$$\text{Residual thrombus ratio} = \frac{\text{Residual fibrin thrombus value}}{\text{Initial fibrin thrombus value}} \times 100$$

Figure 18:
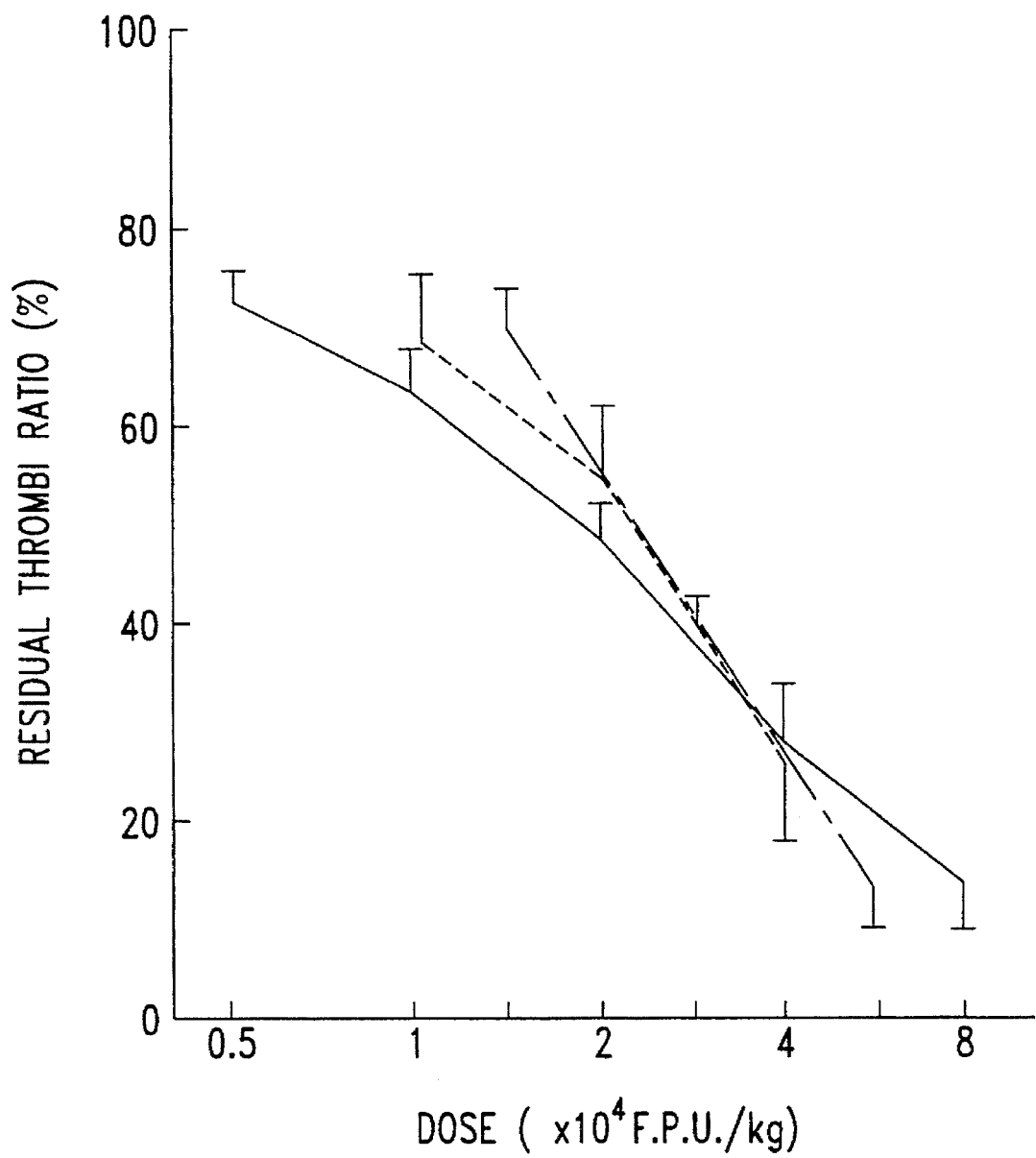
FIG. 18 shows the results of a clot lysis assay on native t-PA and representative t-PA analogs of the present invention. (—) indicates native t-PA, (----) analog #9100, (-..-) analog #9200.

FIG. 18 is a graph of the results obtained using various doses of native t-PA, #9100 and #9200. The data indicate that the mutant proteins are comparable to native t-PA in the ability to lyse clots in vivo.

Figure 19:
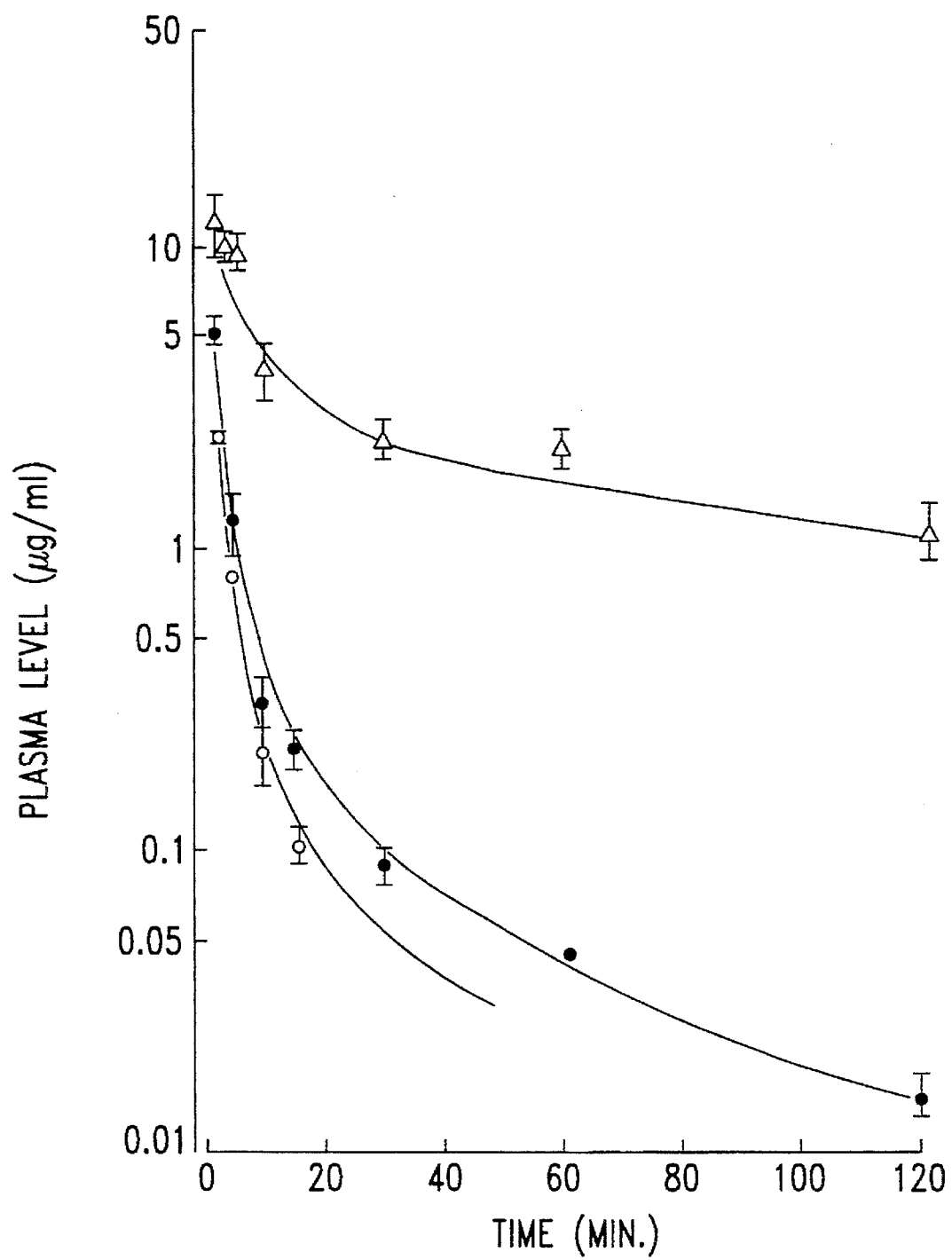
FIG. 19 shows a plot of plasma level vs. time for native t-PA and a representative t-PA analog which were administered to rats. Symbols used are ○, analog 9100; △ analog 9200; and ●, native t-PA.

To assay plasma half-life, proteins were solubilized in a saline solution. The solution was injected into the femoral veins of male Sprague-Dawley rats (230 g to 270 g body weight) at a dose of 0.4 mg/kg. Blood samples (0.5 ml) were removed from the jugular veins, adjusted to 3.8% citric acid, and centrifuged. Levels of t-PA in the plasma were determined using a sandwich-type enzyme immunoassay. FIG. 19 shows a plot of plasma level vs. time after injection.

Changes in plasma levels of the proteins were analyzed by a two-compartment model (Shatgel, L. and Yu, A.B.C., eds., *Applied Biopharmaceutics and Pharmaco-kinetics*, Appleton-Century-Crofts, New York, 1980, pp. 38–48). Half-lives were determined for the alpha and beta phases of clearance. The back extrapolated intercept of the beta phase with the ordinate (B) and the area under the curve (AUC) were also determined. The values obtained are presented in Table 5.

TABLE 5

| Protein | T½(α) | T½(β) | B | AUC |
|---|---|---|---|---|
| Native t-PA | 1.60 | 31.74 | 0.186 | 33.11 |
| 9200 | 2.22 | 153.22 | 1.780 | 462.95 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A human t-PA having a cysteine residue within the growth factor domain at position No. 84 of native t-PA replaced with either serine or alanine.

2. A DNA sequence encoding a human t-PA having a cysteine residue within the growth factor domain at position No. 84 of native t-PA replaced with either serine or alanine.

3. The DNA sequence of claim 2 wherein the amino acid is serine.

4. An expression vector containing a DNA sequence encoding a human t-PA having a cysteine residue within the growth factor domain at position No. 84 of native t-PA replaced with either serine or alanine.

5. The expression vector of claim 4 wherein said vector is Zem99-9100 or Zem99-9200.

6. A host cell transfected or transformed with an expression vector containing a DNA sequence encoding a human t-PA having a cysteine residue within the growth factor domain at position No. 84 of native t-PA replaced with either serine or alanine.

7. The host cell of claim 6 wherein said expression vector is Zem99-9100 or Zem99-9200.

8. The host cell of claim 6 wherein said host cell is *E. coli* or a mammalian host cell.

9. The host cell of claim 8 wherein said mammalian host cells are BHK host cells.

10. The host cell of claim 6 wherein the amino acid is serine.

11. A pharmaceutical composition comprising a human t-PA having a cysteine residue within the growth factor domain at position No. 84 of native t-PA replaced with either serine or alanine, and a pharmaceutically acceptable carrier or diluent.

12. The pharmaceutical composition of claim 11 the amino acid is serine.

* * * * *

UNITED STATES PATENT AND TRADEMARK OFFICE
CERTIFICATE OF CORRECTION

PATENT NO. : 5,486,471
DATED : January 23, 1996
INVENTOR(S) : Eileen R. Mulvihill, et al It is certified that error appears in the above-indentified patent and that said Letters Patent is hereby corrected as shown below:

In column 24, claim 12, line 36, following "11", please insert --wherein--.

Signed and Sealed this

Twenty-eighth Day of May, 1996

Attest:

BRUCE LEHMAN

*Attesting Officer*  *Commissioner of Patents and Trademarks*